(12) United States Patent
Lee et al.

(10) Patent No.: US 8,221,450 B2
(45) Date of Patent: *Jul. 17, 2012

(54) SURGICAL INSTRUMENT

(75) Inventors: Woojin Lee, Hopkinton, MA (US); Andres Chamorro, Medford, MA (US)

(73) Assignee: Cambridge Endoscopic Devices, Inc., Framingham, MA (US)

(*) Notice: Subject to any disclaimer, the term of this patent is extended or adjusted under 35 U.S.C. 154(b) by 1077 days.

This patent is subject to a terminal disclaimer.

(21) Appl. No.: 12/074,378

(22) Filed: Mar. 3, 2008

(65) Prior Publication Data

US 2008/0262537 A1    Oct. 23, 2008

Related U.S. Application Data

(63) Continuation of application No. 11/302,654, filed on Dec. 14, 2005, now Pat. No. 7,338,513, which is a continuation-in-part of application No. 10/822,081, filed on Apr. 12, 2004, now Pat. No. 7,147,650, which is a continuation of application No. 11/242,642, filed on Oct. 3, 2005, now Pat. No. 7,842,028.

(60) Provisional application No. 60/515,560, filed on Oct. 30, 2003, provisional application No. 60/671,189, filed on Apr. 14, 2005.

(51) Int. Cl.
*A61B 17/00* (2006.01)

(52) U.S. Cl. ......................... 606/205; 606/139; 606/167

(58) Field of Classification Search .................. 606/205, 606/139, 167
See application file for complete search history.

(56) References Cited

U.S. PATENT DOCUMENTS

| | | | |
|---|---|---|---|
| 2,028,635 | A | 1/1936 | Wappler |
| 2,507,710 | A | 5/1950 | Grosso |
| 2,790,437 | A | 4/1957 | Moore |
| 3,557,780 | A | 1/1971 | Sato |
| 3,858,577 | A | 1/1975 | Bass et al. |
| 3,895,636 | A | 7/1975 | Schmidt |
| 4,483,562 | A | 11/1984 | Schoolman |
| 4,688,554 | A | 8/1987 | Habib |

(Continued)

FOREIGN PATENT DOCUMENTS

EP    0 095 970 A2    12/1983
(Continued)

OTHER PUBLICATIONS

Nakamura et al., Multi-DOF Forceps Manipulator System for Laparoscopic Surgery—Mechanism Miniaturized & Evaluation of New Enterfaces, 5 pgs.

(Continued)

*Primary Examiner* — Gary Jackson
*Assistant Examiner* — Diane Yabut
(74) *Attorney, Agent, or Firm* — David M. Driscoll, Esq.

(57) ABSTRACT

The surgical instrument includes a distal tool, a rigid or flexible elongated shaft that supports the distal tool, and a proximal handle or control member, where the tool and the handle are coupled to the respective distal and proximal ends of the elongated shaft via distal and proximal bendable motion members. Actuation means extends between said distal and proximal members whereby any deflection of said control handle with respect to said elongated instrument shaft causes a corresponding bending of said distal motion member for control of said working member. A manually rotatable member is arranged adjacent to the control handle for manually rotating the instrument shaft and working member relative to the control handle.

15 Claims, 10 Drawing Sheets

U.S. PATENT DOCUMENTS

| | | | |
|---|---|---|---|
| 4,728,020 A | 3/1988 | Green et al. | |
| 4,763,669 A | 8/1988 | Jaeger | |
| 4,872,456 A | 10/1989 | Hasson | |
| 4,880,015 A | 11/1989 | Nierman | |
| 4,944,093 A | 7/1990 | Falk | |
| 4,944,741 A | 7/1990 | Hasson | |
| 4,945,920 A | 8/1990 | Clossick | |
| 5,002,543 A | 3/1991 | Bradshaw et al. | |
| 5,042,707 A | 8/1991 | Taheri | |
| 5,209,747 A | 5/1993 | Knoepfler | |
| 5,271,381 A | 12/1993 | Ailinger et al. | |
| 5,273,026 A | 12/1993 | Wilk | |
| 5,275,608 A | 1/1994 | Forman et al. | |
| 5,314,424 A | 5/1994 | Nicholas | 606/41 |
| 5,330,502 A | 7/1994 | Hassler et al. | |
| 5,344,428 A | 9/1994 | Griffiths | |
| 5,383,880 A | 1/1995 | Hooven | |
| 5,386,818 A | 2/1995 | Schneebaum et al. | |
| 5,395,367 A | 3/1995 | Wilk | |
| 5,405,344 A | 4/1995 | Williamson et al. | |
| 5,433,721 A | 7/1995 | Hooven et al. | |
| 5,441,494 A | 8/1995 | Ortiz | |
| 5,454,827 A | 10/1995 | Aust et al. | |
| 5,501,654 A | 3/1996 | Failla et al. | |
| 5,520,678 A | 5/1996 | Heckele et al. | |
| 5,599,151 A | 2/1997 | Daum et al. | |
| 5,618,294 A | 4/1997 | Aust et al. | |
| 5,643,294 A | 7/1997 | Tovey et al. | 606/148 |
| 5,702,408 A | 12/1997 | Wales et al. | |
| 5,759,151 A | 6/1998 | Sturges | |
| 5,766,196 A | 6/1998 | Griffiths | |
| 5,772,578 A | 6/1998 | Heimberger et al. | |
| 5,823,066 A | 10/1998 | Huitema et al. | |
| 5,827,177 A | 10/1998 | Oneda et al. | |
| 5,851,208 A | 12/1998 | Trott | |
| 5,855,569 A | 1/1999 | Komi | |
| 5,873,817 A | 2/1999 | Kokish et al. | |
| 5,899,425 A | 5/1999 | Corey, Jr. et al. | |
| 5,899,914 A | 5/1999 | Zirps et al. | |
| 5,904,647 A | 5/1999 | Ouchi | |
| 5,916,146 A | 6/1999 | Allotta et al. | |
| 5,916,147 A | 6/1999 | Boury | |
| 5,921,956 A | 7/1999 | Grinberg et al. | |
| 5,928,263 A | 7/1999 | Hoogeboom | |
| 5,938,678 A | 8/1999 | Zirps et al. | |
| 5,944,713 A | 8/1999 | Schuman | |
| 6,126,633 A | 10/2000 | Kaji et al. | |
| 6,174,280 B1 | 1/2001 | Oneda et al. | |
| 6,210,377 B1 | 4/2001 | Ouchi | |
| 6,210,378 B1 | 4/2001 | Ouchi | |
| 6,270,453 B1 | 8/2001 | Sakai | |
| 6,551,238 B2 | 4/2003 | Staud | |
| 6,623,424 B2 | 9/2003 | Hayakawa et al. | |
| 6,638,214 B2 | 10/2003 | Akiba | |
| 6,656,195 B2 | 12/2003 | Peters et al. | |
| 6,666,854 B1 | 12/2003 | Lange | |
| 6,752,756 B2 | 6/2004 | Lunsford et al. | |
| 6,761,717 B2 | 7/2004 | Bales et al. | |
| 7,090,637 B2 | 8/2006 | Danitz | |
| 7,147,650 B2 | 12/2006 | Lee | 606/205 |
| 7,338,513 B2 * | 3/2008 | Lee et al. | 606/205 |
| 2002/0045803 A1 | 4/2002 | Abe et al. | |
| 2002/0095175 A1 | 7/2002 | Brock et al. | |
| 2002/0133173 A1 | 9/2002 | Brock et al. | |
| 2002/0156497 A1 | 10/2002 | Nagase et al. | |
| 2002/0177750 A1 | 11/2002 | Pilvisto | |
| 2002/0177847 A1 | 11/2002 | Long | |
| 2003/0065359 A1 | 4/2003 | Weller et al. | |
| 2003/0109898 A1 | 6/2003 | Schwarz et al. | |
| 2003/0135204 A1 | 7/2003 | Lee et al | |
| 2003/0149338 A1 | 8/2003 | Francois et al. | |
| 2003/0216618 A1 | 11/2003 | Arai | |
| 2004/0049205 A1 | 3/2004 | Lee et al. | |
| 2004/0111009 A1 | 6/2004 | Adams et al. | |
| 2004/0138529 A1 | 7/2004 | Wiltshire et al. | |
| 2004/0176751 A1 | 9/2004 | Weitzner et al. | |
| 2004/0193146 A1 | 9/2004 | Lee et al. | |
| 2004/0236316 A1 | 11/2004 | Danitz et al. | |
| 2005/0049580 A1 | 3/2005 | Brock et al. | |
| 2005/0107667 A1 | 5/2005 | Danitz et al. | |
| 2005/0228440 A1 | 10/2005 | Brock et al. | |
| 2005/0251112 A1 | 11/2005 | Danitz et al. | |
| 2005/0273084 A1 | 12/2005 | Hinman et al. | |
| 2005/0273085 A1 | 12/2005 | Hinman et al. | |
| 2006/0195097 A1 | 8/2006 | Evans et al. | |
| 2006/0206101 A1 | 9/2006 | Lee | |
| 2006/0270909 A1 | 11/2006 | Davis et al. | |
| 2007/0250110 A1 | 10/2007 | Lu et al. | |

FOREIGN PATENT DOCUMENTS

| | | |
|---|---|---|
| EP | 0 448 284 A2 | 9/1991 |
| EP | 0 626 604 A2 | 5/1994 |
| EP | 0 427 949 B1 | 6/1994 |
| GB | 2 143 920 | 2/1985 |
| WO | WO 90/05491 | 5/1990 |
| WO | WO 92/01414 | 2/1992 |
| WO | WO 94/17965 | 8/1994 |

OTHER PUBLICATIONS

Ryoichi Nakamura et al., Multi-DOF Manipulator System for Laparoscopic Surgery, 8 pgs.

Ryoichi Nakamura et al., Development of Forceps Manipulator System for Laparoscopic Surgery, 6 pgs.

Hiromasa Yamashita et al., "Multi-Slider Linkage Mechanism for Endoscopic Forceps Manipulator," in Proc. of the 2003 IEEE/RSJ, Intl. Conference on Intelligent Robots and Systems, vol. 3, pp. 2577-2582, Las Vegas, Nevada, Oct. 2003.

\* cited by examiner

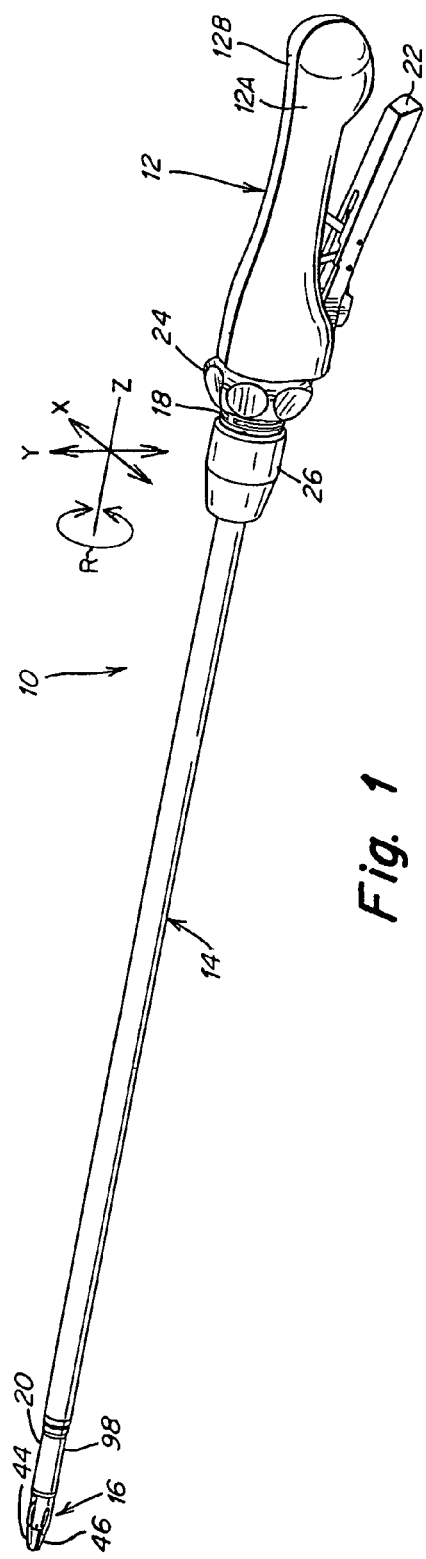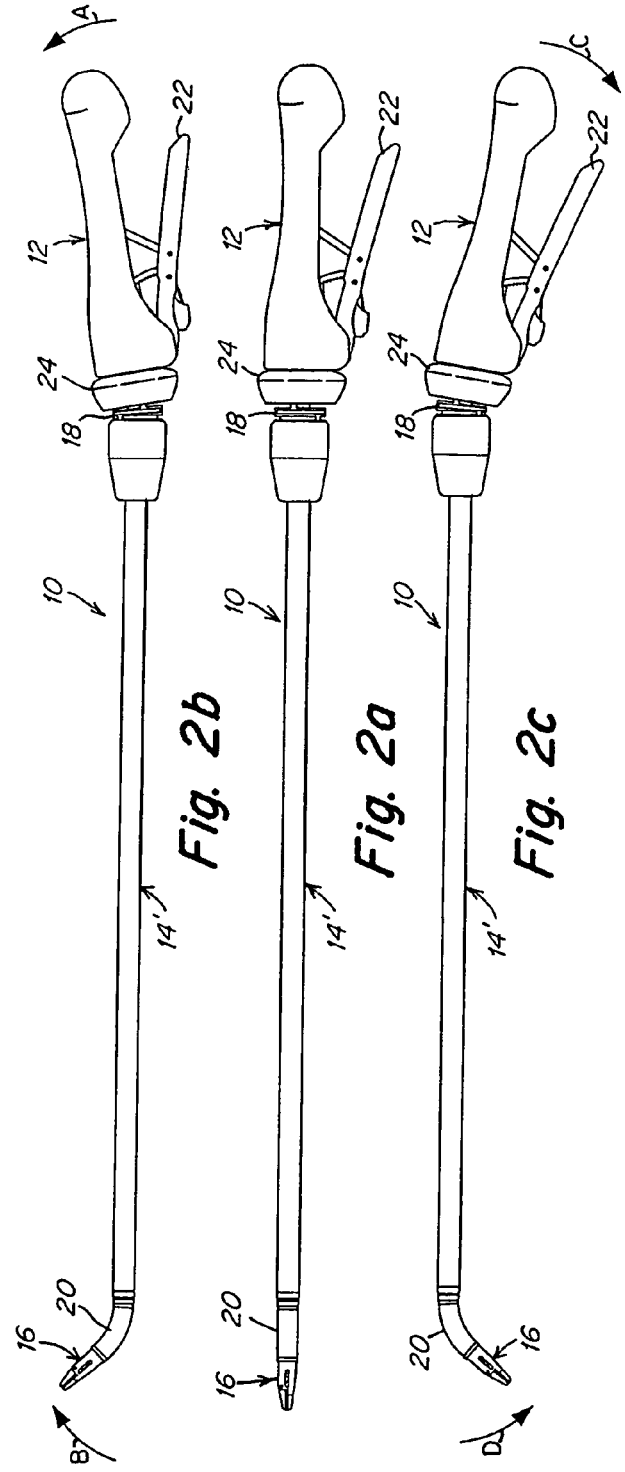
Fig. 1
Fig. 2b  Fig. 2a  Fig. 2c

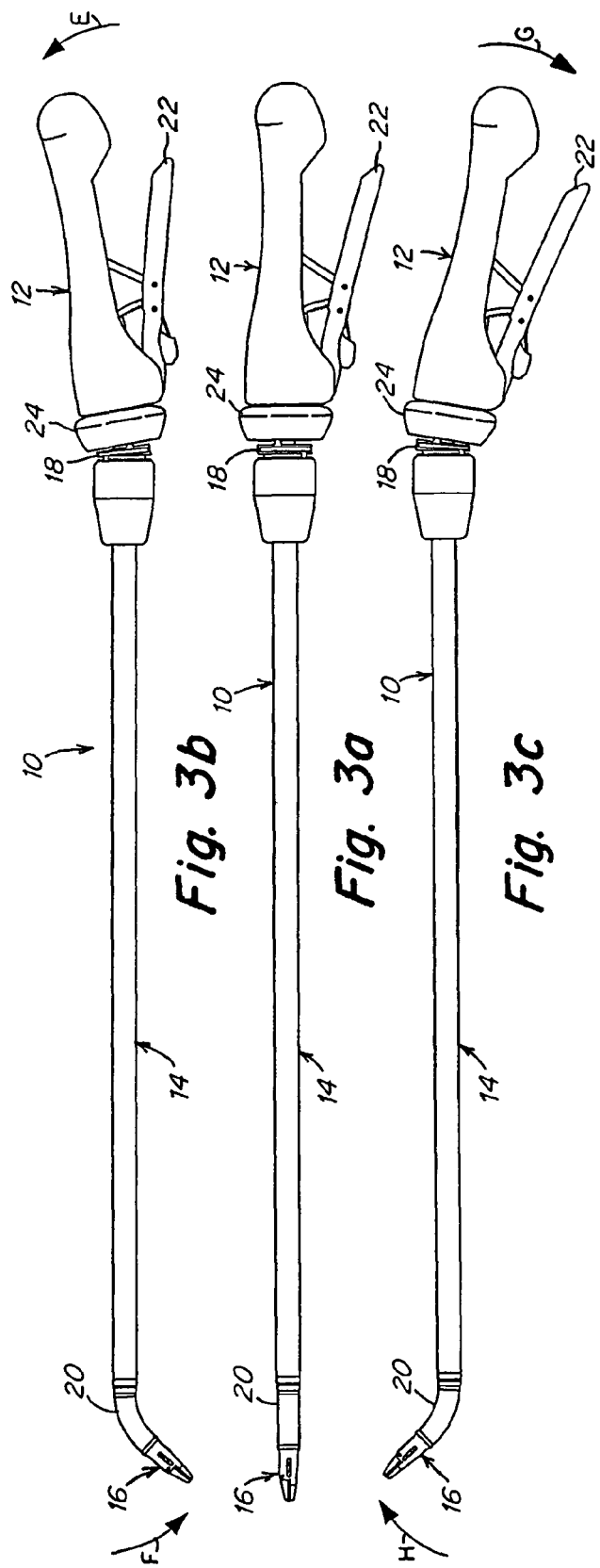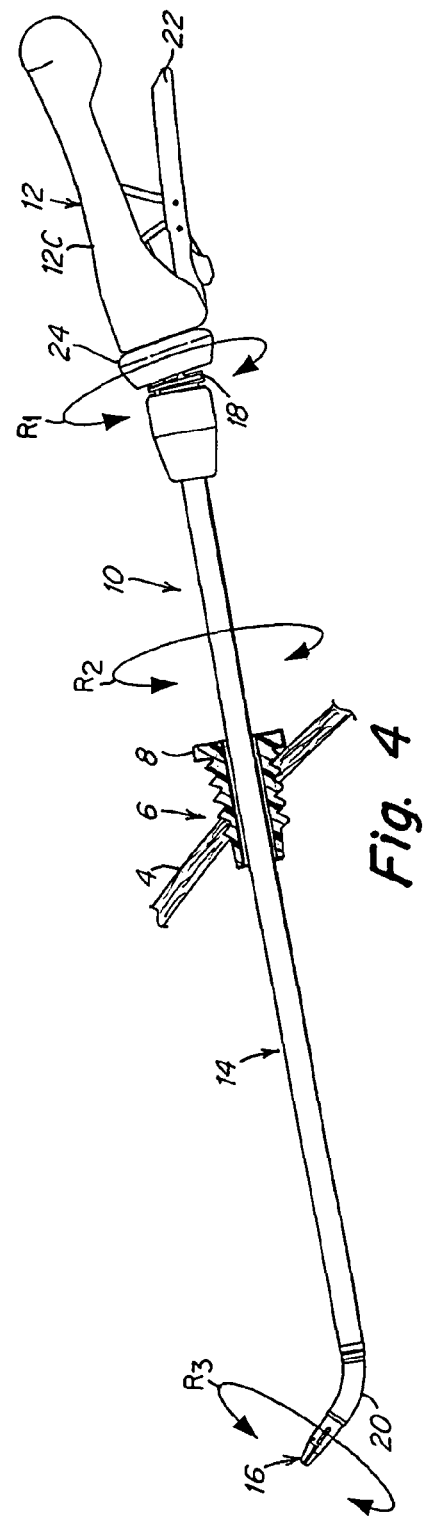

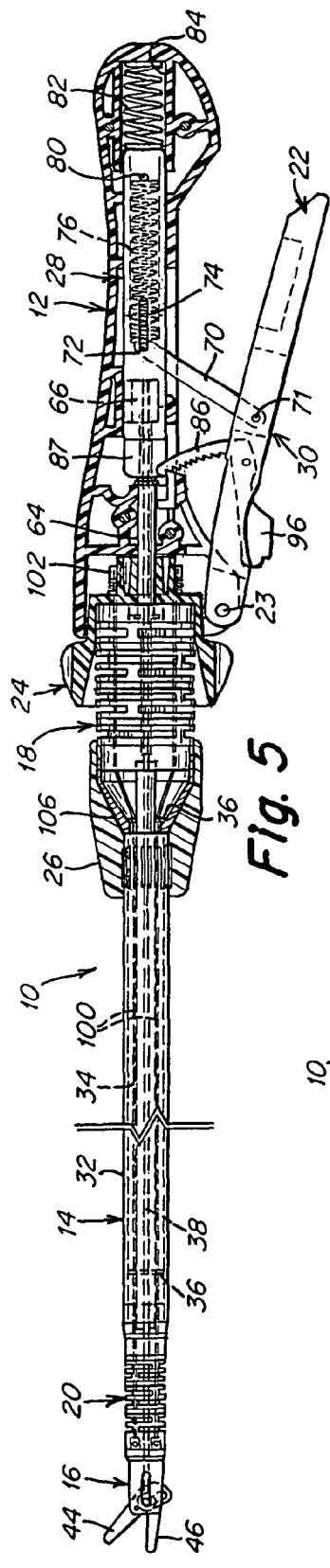

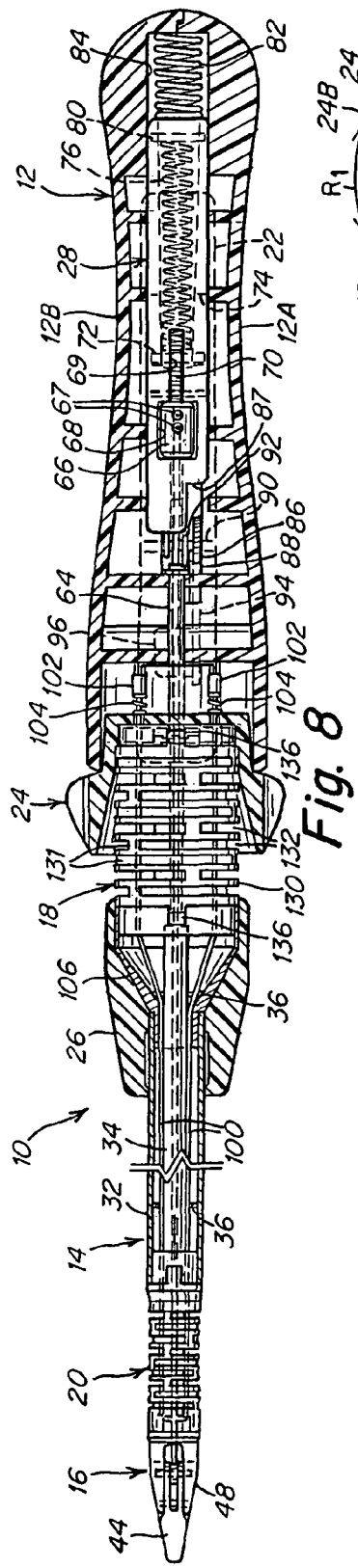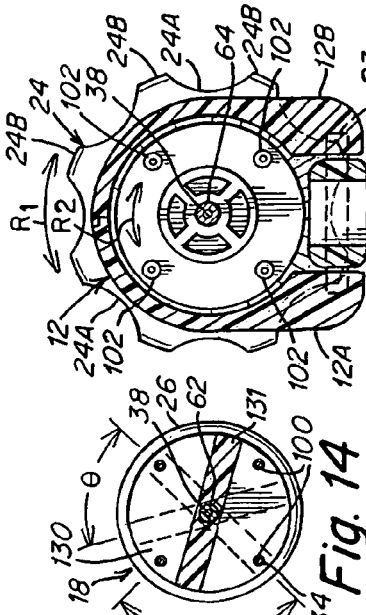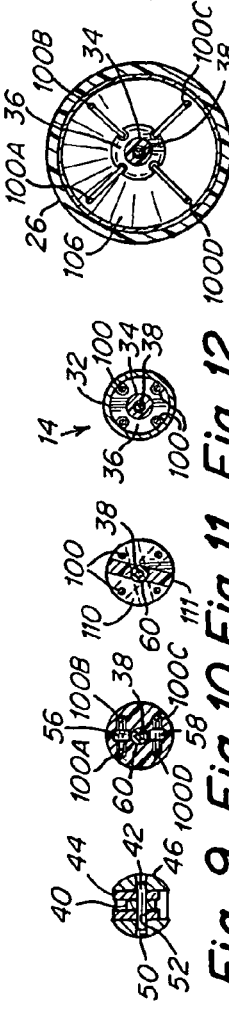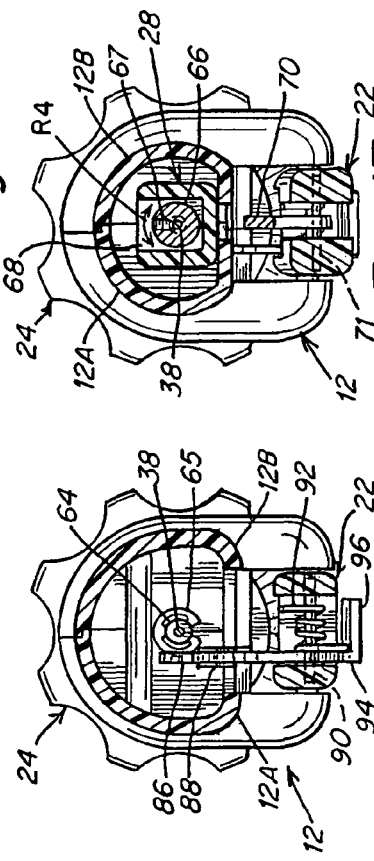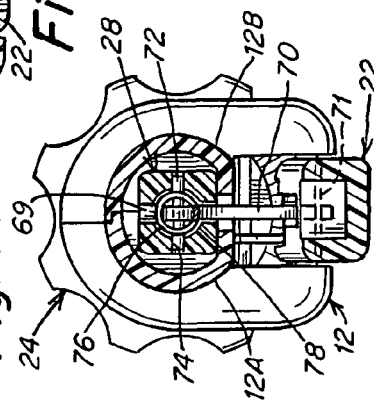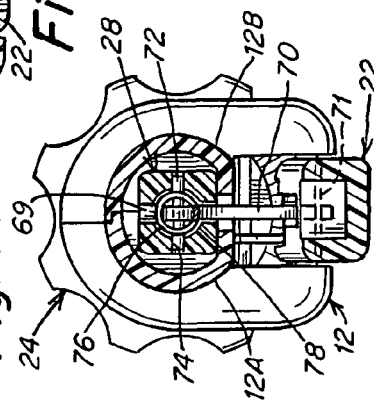

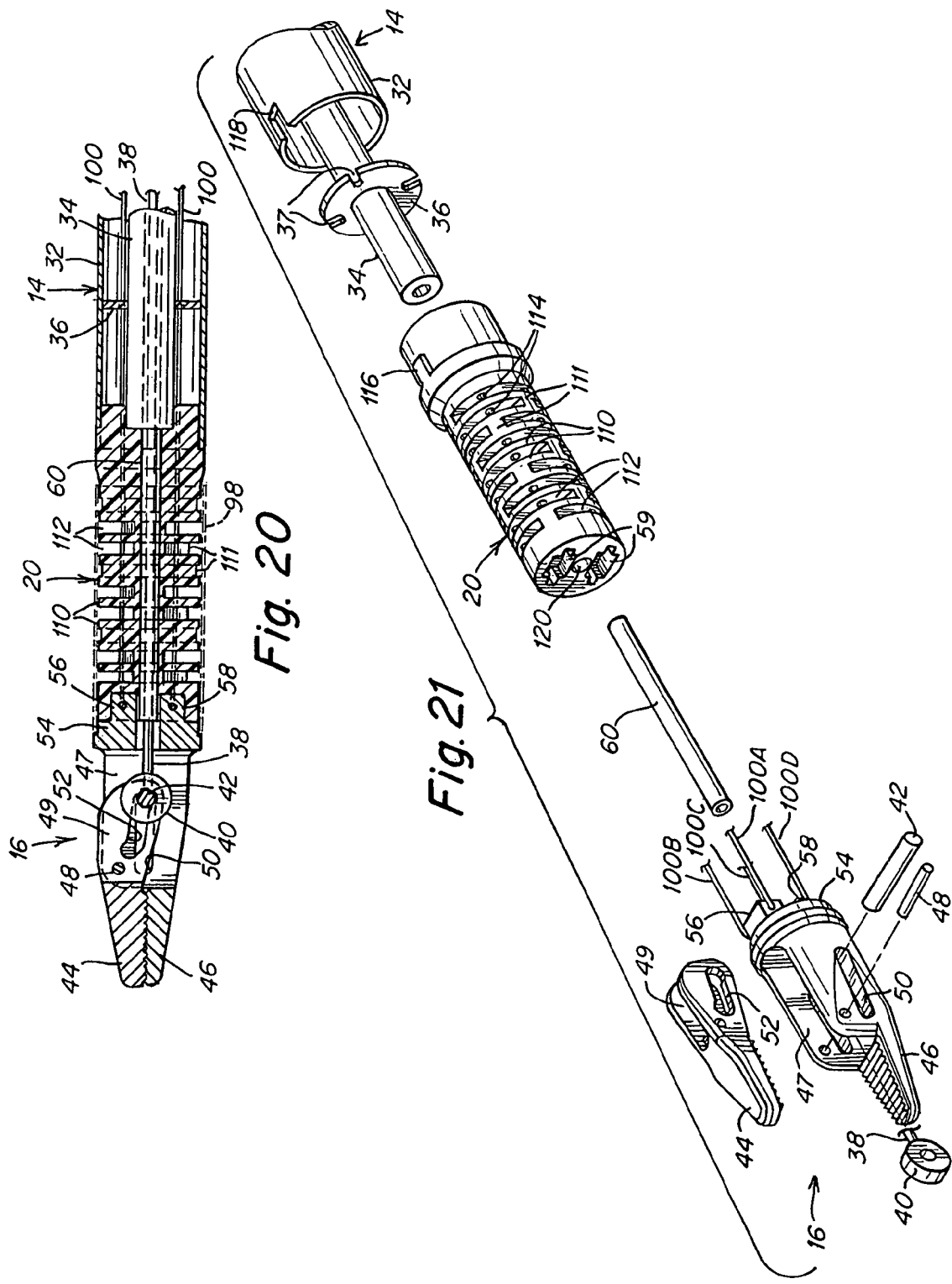

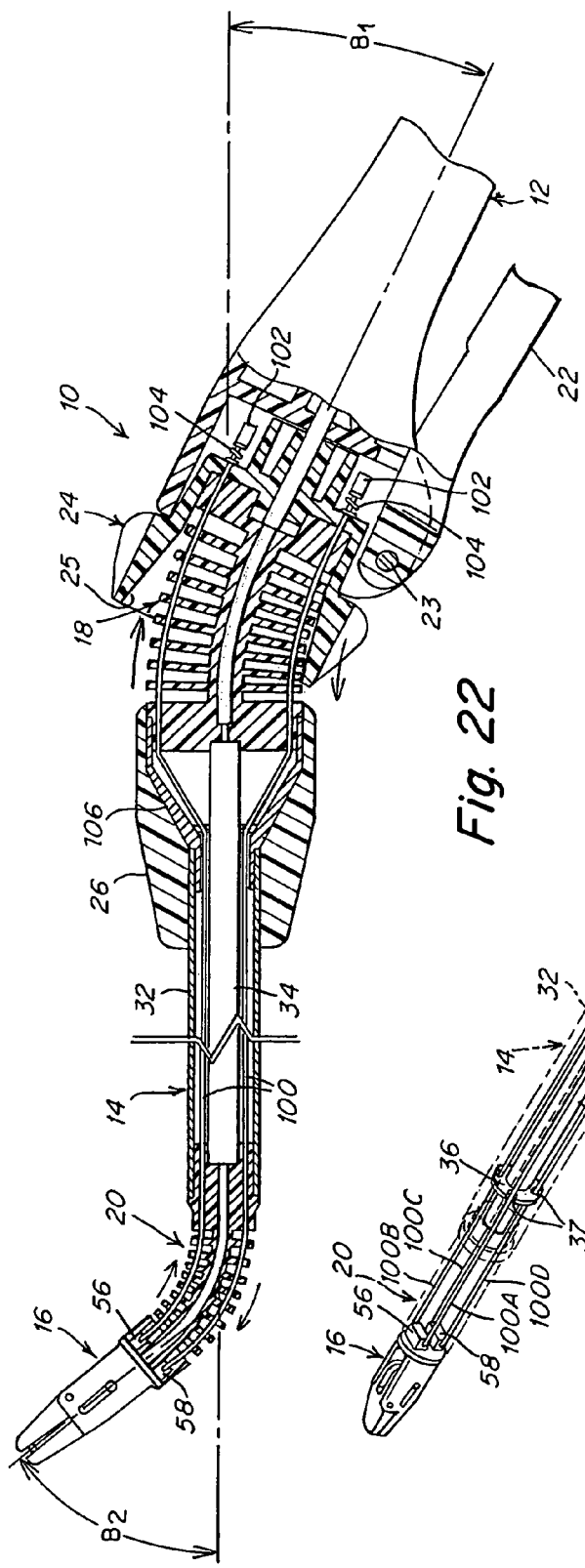
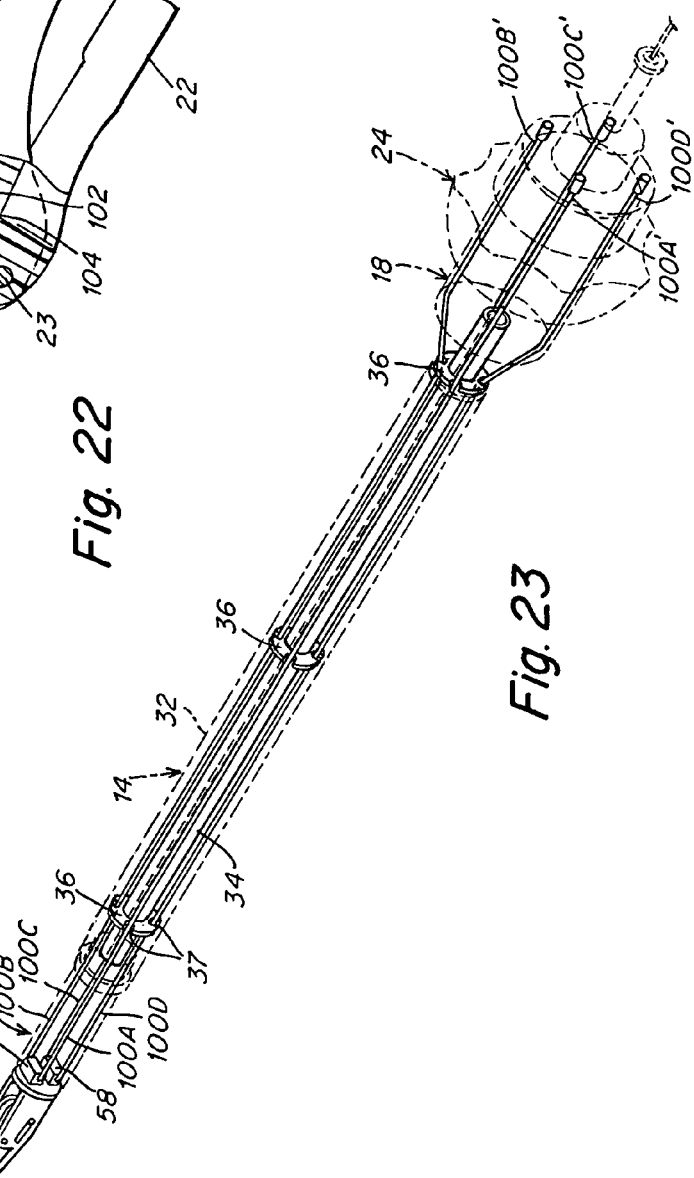
Fig. 22
Fig. 23

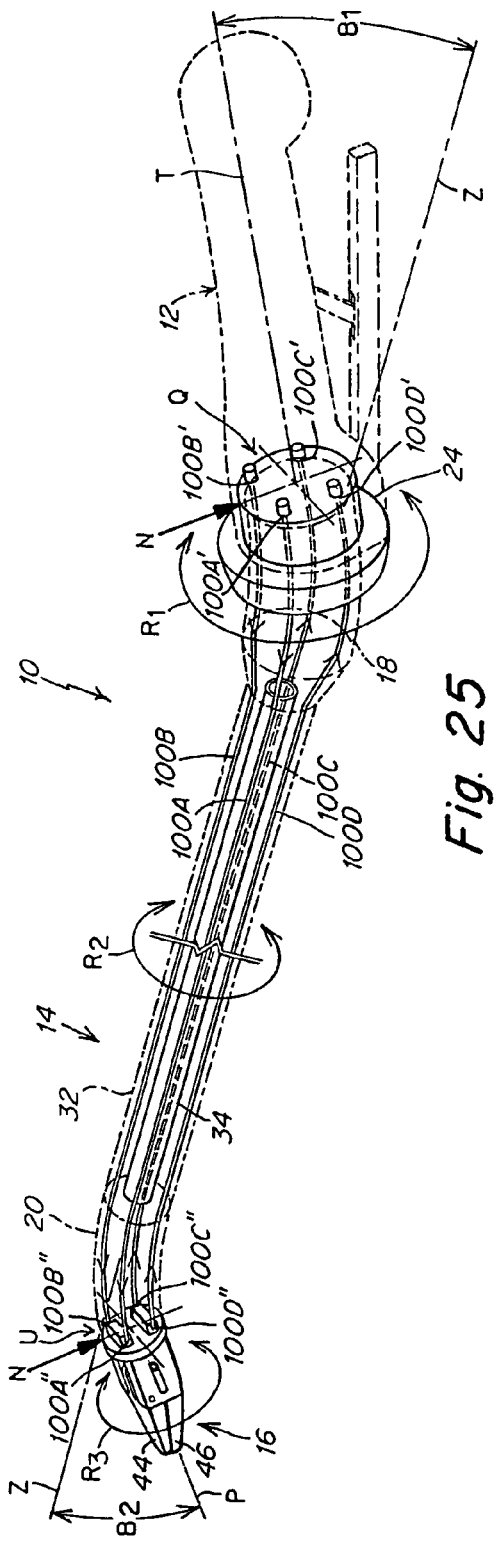
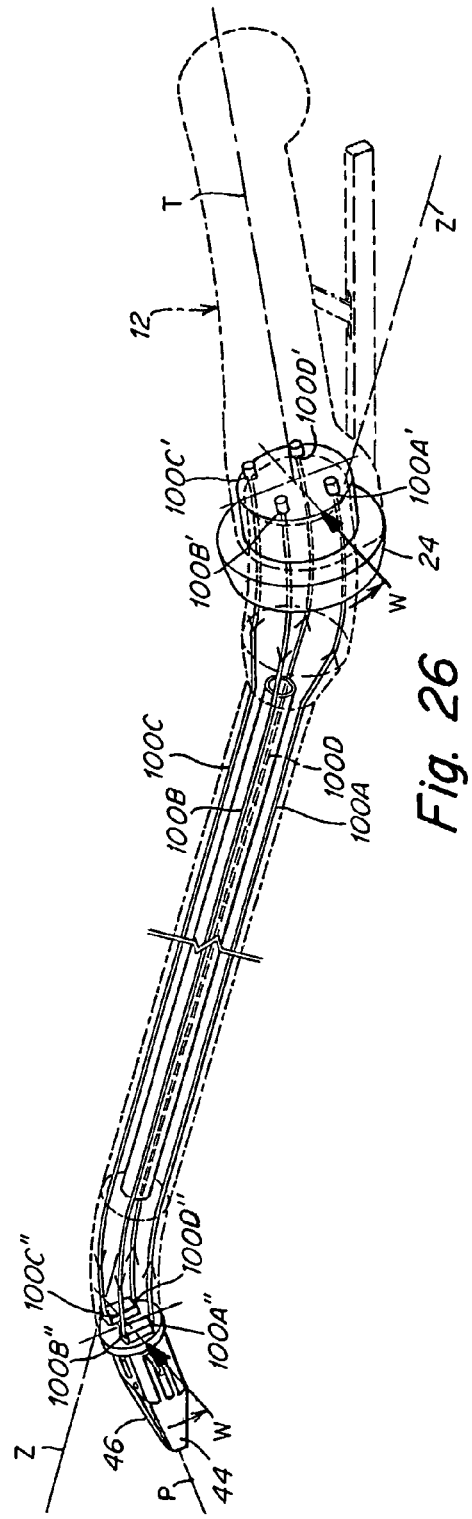
Fig. 25
Fig. 26

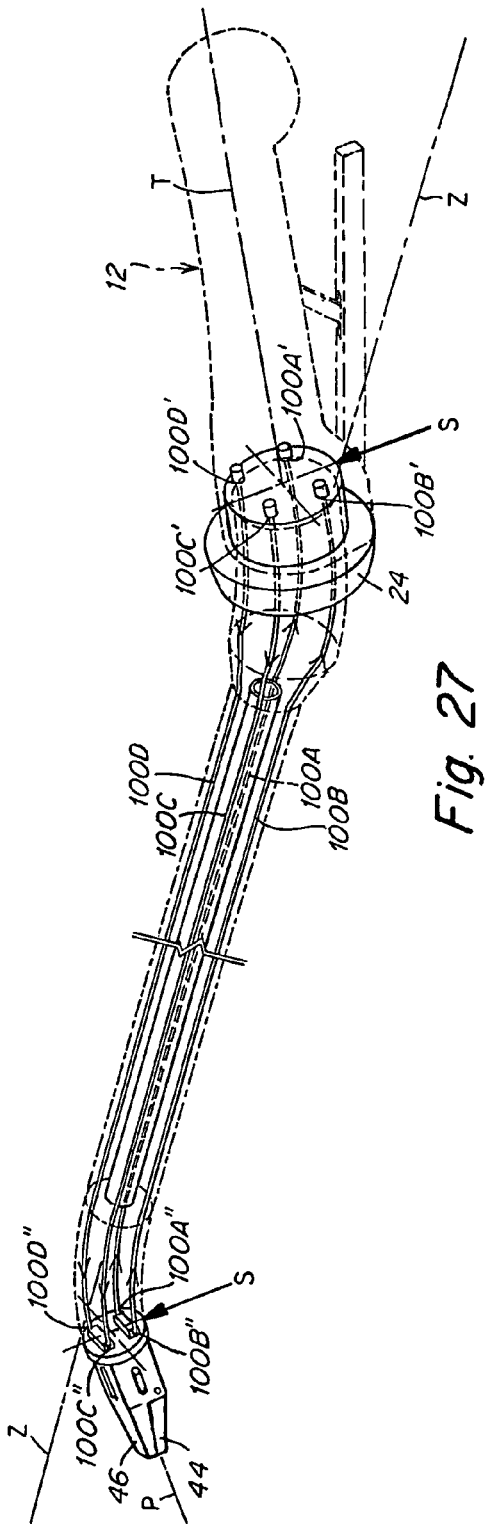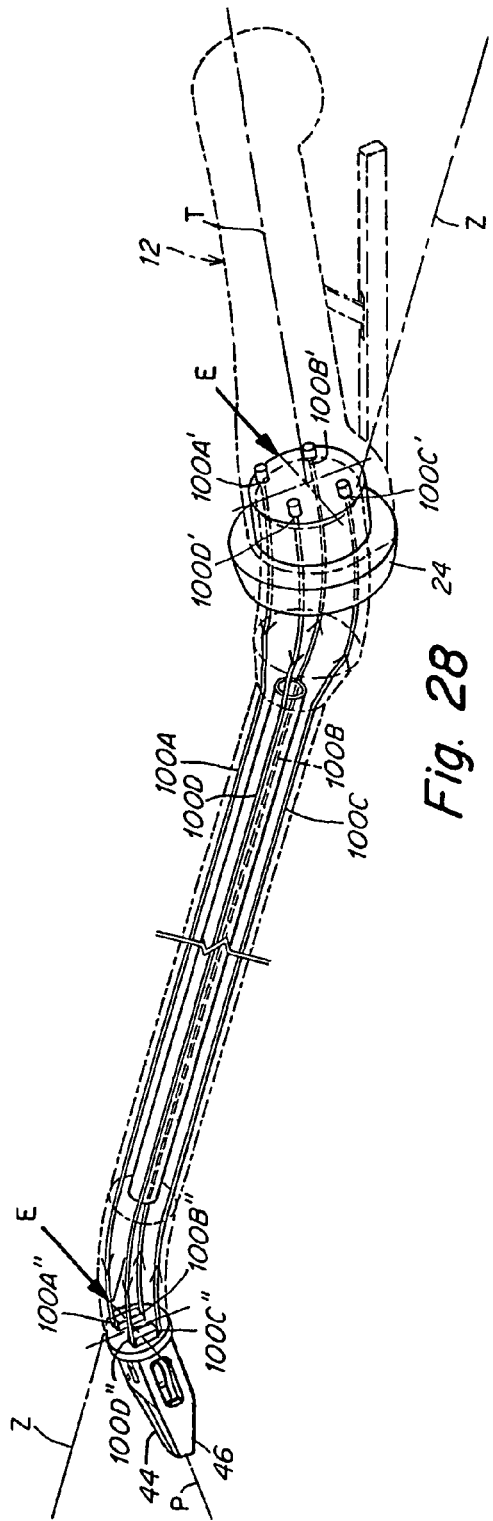

US 8,221,450 B2

SURGICAL INSTRUMENT

RELATED APPLICATIONS

The present invention is a continuation of U.S. application Ser. No. 11/302,654, filed on Dec. 14, 2005, now U.S. Pat. No. 7,338,513 which issued on Mar. 4, 2008 which is a continuation-in-part of earlier filed U.S. application Ser. No. 10/822,081, filed on Apr. 12, 2004, now U.S. Pat. No. 7,147,650 which issued on Dec. 12, 2006 which, in turn, claims priority to U.S. Provisional Application Ser. No. 60/515,560, filed on Oct. 30, 2003. The present application also claims priority to earlier filed U.S. Provisional Application 60/671,189, filed on Apr. 14, 2005. This application is also a continuation of earlier filed U.S. application Ser. No. 11/242,642, filed on Oct. 3, 2005 now U.S. Pat. No. 7,842,028. The content of all of the aforementioned applications are hereby incorporated by reference herein in their entirety.

TECHNICAL FIELD

The present invention relates in general to surgical instruments, and more particularly to manually-operated surgical instruments that are intended for use in minimally invasive surgery or other forms of surgical procedures or techniques. The instrument described herein is for a laparoscopic procedure, however, it is to be understood that the instrument of the present invention can be used for a wide variety of other procedures, including intraluminal procedures.

BACKGROUND OF THE INVENTION

Endoscopic and laparoscopic instruments currently available in the market are extremely difficult to learn to operate and use, mainly due to a lack of dexterity in their use. For instance, when using a typical laparoscopic instrument during surgery, the orientation of the tool of the instrument is solely dictated by the locations of the target and the incision. These instruments generally function with a fulcrum effect using the patients own incision area as the fulcrum. As a result, common tasks such as suturing, knotting and fine dissection have become challenging to master. Various laparoscopic instruments have been developed over the years to overcome this deficiency, usually by providing an extra articulation often controlled by a separately disposed control member for added control. However, even so these instruments still do not provide enough dexterity to allow the surgeon to perform common tasks such as suturing, particularly at any arbitrarily selected orientation.

Accordingly, an object of the present invention is to provide an improved laparoscopic or endoscopic surgical instrument that allows the surgeon to manipulate the tool end of the surgical instrument with greater dexterity.

Another object of the present invention is to provide an improved surgical instrument that has a wide variety of applications, through incisions, through natural body orifices or intraluminally.

SUMMARY OF THE INVENTION

To accomplish the foregoing and other objects and features of this invention, there is provided a surgical instrument that includes an elongated instrument shaft having proximal and distal ends; a working member disposed at the distal end of the instrument shaft; and a control handle disposed at the proximal end of the instrument shaft. The working member is coupled to the distal end of the elongated instrument shaft via a distal motion member, while the control handle is coupled to the proximal end of the elongated instrument shaft via a proximal bendable member. Actuation means extends between the distal and proximal motion members whereby any deflection of the control handle with respect to the elongated instrument shaft causes a corresponding bending of the distal motion member for control of the working member. A manually rotatable member is arranged adjacent the control handle for manually rotating the instrument shaft and working member about their own axes.

In accordance with other aspects of the present invention the actuation means is constructed and arranged so that a motion of the handle causes a like direction motion of the working member, or alternatively the actuation means is constructed and arranged so that a motion of the handle causes an opposite direction motion of the working member. The distal motion member may comprise a distal bendable member and the proximal bendable member is moveable in any direction. The handle may comprises a handle housing and the manually rotatable member may comprise a rotation knob disposed at an open end of the housing. A portion of the proximal bendable member may be disposed in the rotation knob.

In accordance with still other aspects of the present invention, the proximal bendable member may comprise a unitary slotted structure having a plurality of discs separated by slots. The surgical instrument may also include an actuation lever pivotally supported from the handle and an actuator cable intercoupled between the actuation lever and working member. The surgical instrument may also include a ratchet and pawl arrangement coupled to the lever, a slider within a housing of the handle, a link for intercoupling the lever and slider and a release button intercoupled to the ratchet. A pair of springs is provided, one supported in the slider and coupled to the link and the other disposed between the slider and the handle housing.

In accordance with further aspects of the present invention the surgical instrument comprises an elongated instrument shaft having proximal and distal ends; a working member coupled from the distal end of the instrument shaft; a control handle disposed at the proximal end of the instrument shaft; a distal motion means at the distal end of the instrument shaft; a proximal motion means at the proximal end of the instrument shaft; actuation means extending between the distal and proximal means whereby any deflection of the control handle with respect to the elongated instrument shaft causes a corresponding motion of the distal motion means for control of the working member; and means for manually rotating the instrument shaft and working member relative to the control handle.

In accordance with still further aspects of the present invention the distal motion means comprises a distal bendable member and the proximal motion means comprises a proximal bendable member that is moveable in any direction. The handle comprises a handle housing and said means for manually rotating comprises a rotation knob disposed at an open end of the housing. A portion of the proximal bendable member is disposed in a hollow of the rotation knob. The proximal bendable member comprises a unitary slotted structure having a plurality of discs separated by slots and further including a plurality of ribs interconnecting adjacent discs, said ribs being disposed at intervals about the member of 90 degrees or less.

In accordance with another aspect of the present invention there is provided a surgical instrument comprising, an elongated instrument shaft having proximal and distal ends; a working member disposed at the distal end of the instrument shaft; and a control handle disposed at the proximal end of the instrument shaft. The working member is coupled to the distal end of the elongated instrument shaft via a distal motion member while the control handle is coupled to the proximal end of the elongated instrument shaft via a proximal bendable member. Actuation means extends between the distal and proximal members whereby any deflection of the control handle with respect to the elongated instrument shaft causes a corresponding bending of the distal motion member for control of the working member. At least the proximal bendable member may comprise a unitary slotted structure having a plurality of discs separated by slots.

In accordance with another aspect of the present invention the distal motion member also comprises a bendable member formed as a unitary slotted structure having a plurality of discs separated by slots; the proximal bendable member includes a plurality of ribs interconnecting adjacent discs, said ribs being disposed at intervals about the member of less than 90 degrees. The ribs are disposed at an interval on the order of 60 degrees; and further including a manually rotatable member arranged adjacent the control handle for manually rotating the instrument shaft and working member relative to the control handle and about their own axes.

A further embodiment of the invention is a surgical instrument comprising, an elongated instrument shaft having proximal and distal ends; a tool disposed from the distal end of the instrument shaft and supported extending along a distal tool axis; a control handle-disposed from the proximal end of the instrument shaft; a distal bendable member for coupling the distal end of said elongated instrument shaft to the tool; a proximal bendable member for coupling the proximal end of the elongated instrument shaft to the handle; actuation means extending between said distal and proximal bendable members for coupling motion of the proximal motion member to said distal motion member for controlling the positioning of the tool; and a rotation knob adjacent the control handle and rotatable relative to the control handle for causing a corresponding rotation of the tool about the distal tool axis.

In accordance with other aspects of the present invention the proximal bendable member may support the rotation knob so that any rotation imparted to the knob causes a corresponding rotation of the proximal bendable member; the knob may have a cavity for receiving at least a portion of the proximal bendable member; the proximal bendable member may be bendable into a curved configuration and is be fixedly secured with the rotation knob; both the bendable members may be bendable into a curved configuration and any rotation of the rotation knob causes a corresponding rotation of the bendable members, instrument shaft and tool.

Another embodiment of the invention is a manually operated medical instrument having an instrument shaft that couples with an operating handle at a proximal end thereof and a tool at a distal end thereof. The instrument further comprises a proximal bendable member at the proximal end of the instrument shaft that is bendable into a curved configuration, a distal bendable member at the distal end of the instrument shaft that is bendable into a curved configuration, and one or more actuating elements intercoupling the proximal and distal bendable members responsive to a manually initiated bending at the proximal bendable member to cause a corresponding bending into a curved configuration of the distal bendable member so as to control, via the handle, the positioning of the tool.

In accordance with still other aspects of the present invention the bendable members may be bendable in all directions; the bendable members may be bendable in any direction; the proximal bendable member may be manipulated in any direction do that the distal bendable member is controlled in three dimensions; a rotation knob may be disposed between the handle and proximal bendable member; the rotation knob may be supported to rotate the proximal bendable member therewith; the rotation of the rotation knob controls the tool for corresponding rotation about a tool axis; the tool may be disposed from the distal bendable member along a longitudinal distal tool axis, the rotation of the rotation knob causing a corresponding rotation of the tool about the distal tool axis; one or more actuating elements comprises a set of actuation cables and wherein at least one of the set is in tension while at least another one thereof is in relaxation; four cables may be disposed at 90 degree intervals about the instrument shaft with two in tension and two in relaxation during a bending and wherein the instrument shaft comprises an elongated instrument shaft extending along a longitudinal axis and wherein the distal bendable member is disposed in-line with the elongated instrument shaft coupling a distal end of the elongated instrument shaft to the tool and wherein the proximal bendable member is disposed in line with the elongated instrument shaft coupling a proximal end of the elongated instrument shaft via the rotation knob to the handle.

Another embodiment of the invention is a surgical instrument comprising: an elongated instrument shaft having proximal and distal ends; a working member disposed from the distal end of the instrument shaft; and a control handle disposed from the proximal end of the instrument shaft. A distal bendable member is capable of bending into a curved configuration, the working member being coupled to the distal end of the elongated instrument shaft via the distal bendable member; a proximal bendable member is capable of bending into a curved configuration, the control handle coupled to the proximal end of the elongated instrument shaft via a proximal bendable member. A manually rotatable member is arranged adjacent the control handle and between the control handle and proximal bendable member. The rotatable member is adapted to be manually rotated to, in turn, rotate the instrument shaft, distal bendable member and working member relative to the control handle. An actuation element extends between the distal and proximal bendable members whereby any deflection of the control handle with respect to the elongated instrument shaft causes a corresponding bending of the distal motion member for control of the working member.

In accordance with other aspects of the present invention the rotatable member comprises a rotation knob having a cavity for receiving at least a portion of the proximal bendable member therein and at least a portion of the rotation knob is received by the handle in an open end of the handle, the rotation knob having the proximal bendable member supported therein and in a fixed relative rotation with respect to the proximal bendable member the working member may comprise a tool that is supported from the distal bendable member extending along a distal tool axis and the rotatable member may comprise a rotation knob, the rotation of the rotation knob causing a rotation of the working member about the distal tool axis. The rotation of the rotation knob rotates the instrument shaft and distal bendable member, rotating the tool about the distal tool axis while maintaining the orientation of the tool.

BRIEF DESCRIPTION OF THE DRAWINGS

It should be understood that the drawings are provided for the purpose of illustration only and are not intended to define the limits of the disclosure. The foregoing and other objects and advantages of the embodiments described herein will become apparent with reference to the following detailed description when taken in conjunction with the accompanying drawings in which:

FIG. 1 is a perspective view of a preferred embodiment of the surgical instrument of the present invention;

FIGS. 2a, 2b and 2c are sequential side views of one embodiment of the surgical instrument wherein the distal bendable member bends in the same direction as the proximal bendable member;

FIGS. 3a, 3b and 3c are sequential side views of another embodiment of the surgical instrument wherein the distal bendable member bends in the opposite direction to the proximal bendable member;

FIG. 4 is a schematic side view of the surgical instrument depicted in FIGS. 1-3 illustrating the instrument extending through an incision and adapted to be controlled by a surgeon to roll the instrument tool about its longitudinal or Z axis;

FIG. 5 is a longitudinal cross-sectional side view of the surgical instrument of FIG. 1 with a handle position corresponding to the jaws being in a fully open position;

FIG. 6 is a longitudinal cross-sectional side view as depicted in FIG. 5 further illustrating the jaws being closed upon a needle;

FIG. 7 is a fragmentary cross-sectional view of the handle assembly of the surgical instrument of FIG. 1 and further illustrating the jaw actuation means exerting a pressure at the jaws;

FIG. 8 is a cross-sectional plan view taken along line 8-8 of FIG. 6 and illustrating the jaw actuation means exerting a pressure on the jaws;

FIG. 9 is a cross-sectional view taken along line 9-9 of FIG. 6 showing the camming means for the moveable jaw;

FIG. 10 is a cross-sectional view taken along line 10-10 of FIG. 6 showing the flex cable anchors;

FIG. 11 is a cross-sectional view taken along line 11-11 of FIG. 6 showing the distal flexible or bendable member and cables passing therethrough;

FIG. 12 is a cross-sectional view taken along line 12-12 of FIG. 6 showing the instrument shaft portion of the instrument and cables passing therethrough;

FIG. 13 is a cross-sectional view taken along line 13-13 of FIG. 6 showing the cable transition from the instrument shaft to the proximal bendable member;

FIG. 14 is a cross-sectional view taken along line 14-14 of FIG. 6 showing further details of the proximal bendable member and cable passages;

FIG. 15 is a cross-sectional view taken along line 15-15 of FIG. 6 showing the proximal end of the rotation member or knob;

FIG. 16 is a cross-sectional view taken along line 16-16 of FIG. 6 showing the ratchet and pawl locking action for the spring tensioning of the tool actuator cable;

FIG. 17 is a cross-sectional view taken along line 17-17 of FIG. 6 showing the rotating barrel means to prevent torsional forces on the tool actuator cable;

FIG. 18 is a cross-sectional view taken along line 18-18 of FIG. 6 showing the spring loading means for the tool actuator cable;

FIG. 20 is a somewhat enlarged cross-sectional view of the distal end of the surgical instrument as taken along line 20-20 of FIG. 19;

FIG. 21 is an exploded perspective view of the distal end of the surgical instrument as shown in FIG. 20;

FIG. 22 is a schematic side cross-sectional view of the instrument type described in FIGS. 3a-3c including the cabling and actuation;

FIG. 23 is a schematic perspective view illustrating the cabling of FIG. 22;

FIGS. 25-28 are sequential perspective schematic views illustrating the cable arrangement for different rotational positions.

DETAILED DESCRIPTION OF THE PREFERRED EMBODIMENT

The instrument of the present invention may be used to perform minimally invasive procedures. "Minimally invasive procedure," refers herein to a surgical procedure in which a surgeon operates through small cut or incision, the small incision being used to access the operative site. In one embodiment, the incision length ranges from 1 mm to 20 mm in diameter, preferably from 5 mm to 10 mm in diameter. This procedure contrasts those procedures requiring a large cut to access the operative site. Thus, the flexible instrument is preferably used for insertion through such small incisions and/or through a natural body lumen or cavity, so as to locate the instrument at an internal target site for a particular surgical or medical procedure. The introduction of the surgical instrument into the anatomy may also be by percutaneous or surgical access to a lumen or vessel, or by introduction through a natural orifice in the anatomy.

In addition to use in a laparoscopic procedure, the instrument of the present invention may be used in a variety of other medical or surgical procedures including, but not limited to, colonoscopic, upper GI, arthroscopic, sinus, thoracic, transvaginal and cardiac procedures. Depending upon the particular procedure, the instrument shaft may be rigid, semi-rigid or flexible.

Although reference is made herein to a "surgical instrument," it is contemplated that the principles of this invention also apply to other medical instruments, not necessarily for surgery, and including, but not limited to, such other implements as catheters, as well as diagnostic and therapeutic instruments and implements.

Figure 24:
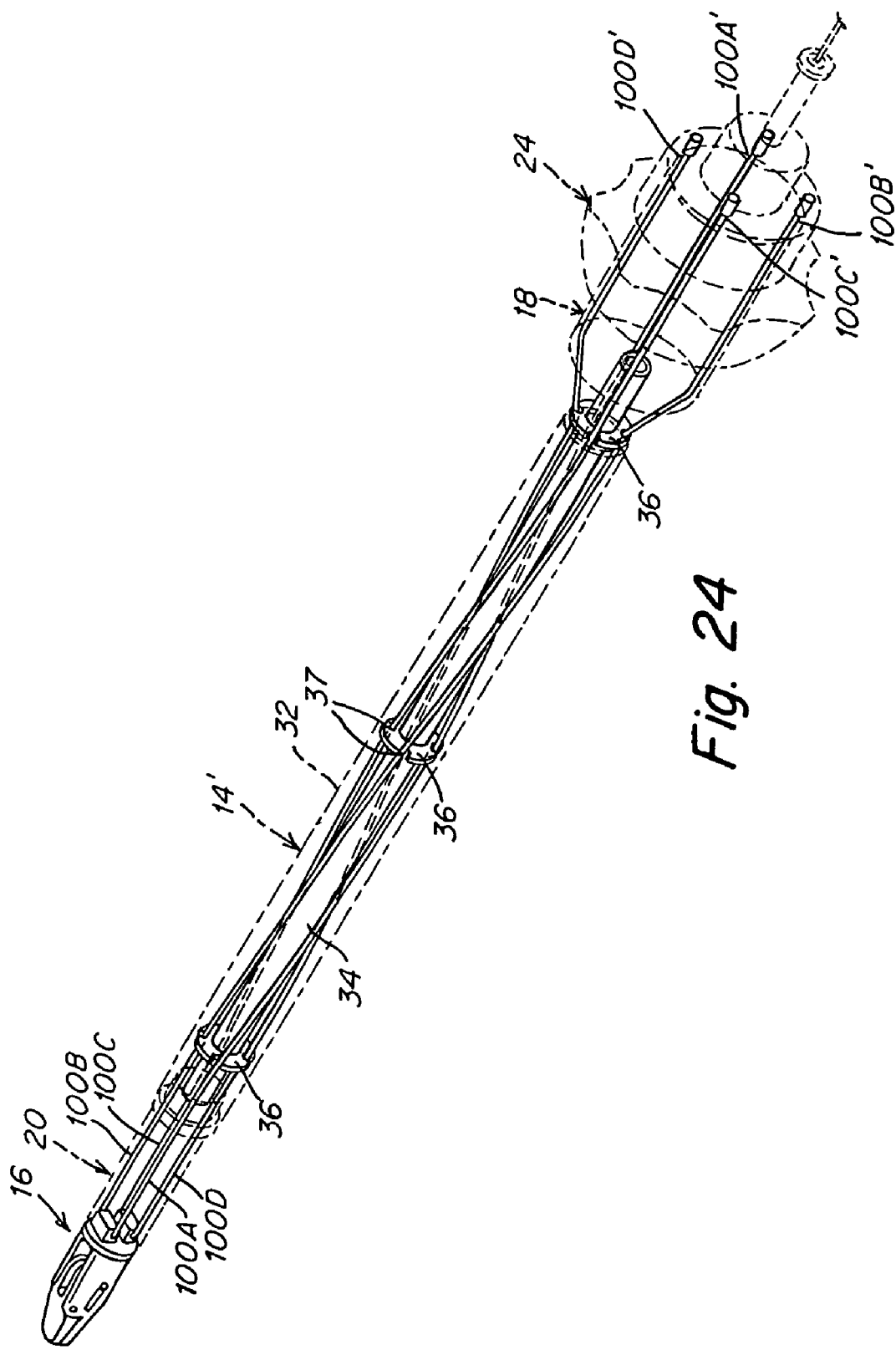
FIG. 24 is a schematic perspective view of an alternate cabling scheme such as used in the embodiment of FIGS. 2a-2c.

FIG. 1 is a perspective view of a preferred embodiment of the surgical instrument 10 of the present invention. In this surgical instrument both the tool and handle motion members or bendable members are capable of bending in any direction, thus enabling three dimensional tool positioning. They are interconnected via cables in such a way that a bending action at the proximal member provides a related bending at the distal member. As will be described in further detail hereinafter, the proximal member is preferably larger than the distal member so as to provide enhanced ergonomic control. FIGS. 2a-2c show a bending action in which the distal bendable member bends in the same direction as the proximal bendable member. FIGS. 3a-3c show an alternate embodiment in which the bendable or flexible members are adapted to bend in opposite directions. FIG. 23 is a schematic perspective view illustrating the cabling that corresponds to the action depicted in FIGS. 3a-3c. FIG. 24 is a schematic perspective view illustrating the cabling that corresponds to the action depicted in FIGS. 2a-2c.

It should be noted that the amount of bending motion produced at the distal bending member is determined by the dimension of the proximal bendable member in comparison to that of the distal bendable member. In the disclosed embodiment the proximal bendable member is approximately three times the diameter of the distal bendable member, and as a result, the motion produced at the distal bendable member is about three times the magnitude of the motion at the proximal bendable member. Although FIGS. 2 and 3 show only the side view where only pitch motion is illustrated, it should be noted that the proximal bendable member can be bent in any direction controlling the distal bendable member to bend in either the same or an opposite direction, but in the same plane. As a result, as depicted in FIG. 4 the surgeon is able to roll the instrument's tool about its longitudinal axis at any orientation simply by rolling the axial rotation knob 24.

In this description reference is made to bendable members. These members may also be referred to as turnable members or flexible members. In the descriptions set out herein, terms such as "bendable section," "bendable segment," "bendable motion member," or "turnable member" refer to an element of the instrument that is controllably bendable in comparison to an element that is pivoted at a joint. The bendable elements of the present invention enable the fabrication of an instrument that can bend in any direction without any singularity and that is further characterized by a ready capability to bend in any direction, all with a single unitary or uni-body structure. A definition of these bendable motion members is—an instrument element, formed either as a controlling means or a controlled means, and that is capable of being constrained by tension or compression forces to deviate from a straight line to a curved configuration without any sharp breaks or angularity—.

Referring to FIG. 1, the surgical instrument 10 is comprised of a handle 12 at the proximal end of the instrument, an elongated instrument shaft 14 and a tool or end effector 16 disposed at the distal end of the surgical instrument. In the disclosed embodiment the instrument shaft 14 is rigid, usually of a metal material, although it may also be constructed so as to be at least partially flexible or bendable. For normal laparoscopic procedures the instrument shaft 14 is usually rigid. For an example of a flexible instrument shaft used intraluminally refer herein to FIGS. 14 and 15 of related U.S. application Ser. No. 10/822,081, filed on Apr. 12, 2004 which is hereby incorporated by reference herein in its entirety.

In FIG. 1 the handle 12 is illustrated as comprised of two handle halves 12A and 12B. A lever 22 is manipulatable by the surgeon for opening and closing the end effector 16 at the distal end of the instrument shaft 14. In FIG. 1 the end effector is illustrated as comprised of a movable jaw 44 and a fixed jaw 46. The rotation knob 24 at the proximal end of the instrument is used to rotate the entire instrument shaft and end effector. This rotation is illustrated in FIG. 1 by the circular arrow R. Also note in FIG. 1 the illustration of a coordinate system expressed by the X-Y-Z axes. The roll of the instrument indicated by the arrow R is about the Z axis. The Z axis corresponds to the longitudinal axis of the shaft 14 of the instrument 10. FIG. 1 also illustrates an adaptor cover 26 for partially retaining a portion of the proximal bendable member 18. At the distal end of the instrument shaft 14, there is provided the distal bendable member 20. In FIG. 1 this is illustrated at least partially covered by the cover 98. The cover 98 may be a thin plastic or rubber flexible tube that readily deflects as the distal bendable member is actuated from the proximal bendable member. For instruments such as a needle holder or a suture assist device, the compliant cover 98 is beneficial in preventing the suture from catching while tying a knot. However, for other applications one may choose not to use the cover 98 so as to simplify the instrument and its fabrication. Other components, such as the knob 24, cover 26 and bendable members are formed of a plastic material.

The instrument of the present invention is preferably constructed to be disposable or alternatively responsible. Accordingly, to make the instrument as inexpensively as possible most of the components are made of a plastic material.

FIGS. 2a-2c depict one embodiment for the surgical instrument in which the handle and end effector are controlled to turn or bend in the same direction. If the handle is turned upwardly then the tool turns upwardly and vice-versa. FIG. 2a shows the handle in a straight position and the corresponding tool in a likewise straight position. FIG. 2b illustrates the handle end of the instrument having been moved upwardly in the direction of arrow A. This causes a corresponding movement upwardly of the end effector 16 in the direction of arrow B. Similarly, FIG. 2c illustrates the handle 12 being moved downwardly in the direction of arrow C causing a corresponding movement downwardly of the end effector 16 in the direction of arrow D. The bending forces depicted in FIGS. 2b and 2c are imposed upon the proximal bendable member 18 and when that is bent or turned, this causes a corresponding bending or turning of the distal bendable member so as to orient the end effector. The bending forces are imposed at the handle of the instrument by the surgeon. Also, although FIGS. 2a-2c only depict "up" and "down" movement essentially in the plane of the paper, it is understood that the handle can be actuated in any direction including planes in and out of the paper.

FIGS. 3a-3c depict a different embodiment of the surgical instrument. In this embodiment, the bending of the handle portion of the instrument causes an opposite direction bending of the end effector. In FIG. 3a the handle is shown in a straight position and the end effector is also shown in a straight position. In FIG. 3b the handle 12 has been moved upwardly in the direction of arrow E causing a corresponding movement downwardly of the end effector 16 in the direction of arrow F. In FIG. 3c the handle 12 is shown being bent or turned to a downward position as illustrated by the arrow G. This causes a corresponding bending or turning up of the end effector 16 in the direction depicted by arrow H.

As with the embodiment of FIGS. 2a-2c, in the FIGS. 3a-3c the translation of the bending force at the handle end of the instrument is transferred to the distal end of the instrument. This occurs by way of the proximal bendable member 18 controlled by the user from the handle 12 and, in turn, controlling the distal bendable member 12 which, in turn, controls the positioning and orientation of the end effector 16. Also, although FIGS. 3a-3c only depict "up" and "down" movement essentially in the plane of the paper, it is understood that the handle can be actuated in any direction including planes in and out of the paper.

FIG. 4 depicts the surgical instrument 10 in position, as may occur during a surgical procedure. For example, the instrument may be used for laparoscopic surgery through the abdominal wall 4. For this purpose there is provided an insertion site 6 at which there is disposed a cannula or trocar 8. The shaft of the instrument 14 is adapted to pass through the cannula 8 so as to dispose the distal end of the instrument at an operative site. The end effector 16 is depicted in FIG. 4 at such an operative site. FIG. 4 also depicts the rolling motion that can be carried out with the instrument of the present invention. This can occur by virtue of the rotation of the rotation knob 24 relative to the handle 12. This is illustrated in FIG. 4 by the circular arrow R1. When the rotation knob 24 is rotated, in either direction, this causes a corresponding rotation of the instrument shaft 14. This is depicted in FIG. 4 by the rotational arrow R2. This same motion also causes a rotation of the end effector 16 as illustrated by the rotational arrow R3 in FIG. 4.

The combination of manipulation via the bendable members and the rotation via the knob 24 provides a very precise and ergonomically comfortable degree of control for the surgeon. The instrument is adapted to be held in a number of different ways in use. In one technique, the instrument handle may be grasped so that the middle, ring and small fingers are about the surface 12C while the thumb engages the lever 22 and release button 96. The index finger may extend to engage the rotation knob 24. In this way all manipulations can be easily coordinated by the surgeon with one hand. The instrument may also be grasped in the following manner. The thumb may rest on the surface 12C while the fingers grasp the lever 22. The index finger may manipulate the knob 24. The thumb may also assist in manipulating the knob 24.

In the drawings a set of jaws is depicted, however, other tools or devices may be readily adapted for use with the instrument of the present invention. These include, but are not limited to, cameras, detectors, optics, scope, fluid delivery devices, syringes, etc. The tool may include a variety of articulated tools such as: jaws, scissors, graspers, needle holders, micro dissectors, staple appliers, tackers, suction irrigation tools and clip appliers. In addition, the tool may include a non-articulated tool such as: a cutting blade, probe, irrigator, catheter or suction orifice.

Reference is now made to FIGS. 5-22 for further details of the instrument 10 depicted in FIG. 1. The instrument that is depicted in FIGS. 5-22 is the embodiment illustrated in FIGS. 3a-3c. In this particular embodiment the cabling within the instrument shaft is maintained in a straight configuration such as illustrated in FIG. 23. Alternate cabling is described in FIG. 24 corresponding to the embodiment of FIGS. 2a-2c.

As indicated previously, the end effector or tool 16 is actuated by means of the jaw actuation means 30 which is comprised primarily of the elongated lever 22. The lever 22 is supported from the housing at the lever pivot pin 23. Refer to FIGS. 5-7 and 19. The closing of the lever 22 against the handle 12 acts upon the slider 28 which is used to capture the very proximal end of the actuation cable 38. When the slider 28 is in the position depicted in FIG. 5, it is noted that the end effector jaws are fully open. When the slider is moved toward the right as depicted in FIG. 6, then the jaws 44 and 46 are moved toward a closed position. In FIG. 6 the jaws are illustrated as closing so as to grasp a needle 45.

The instrument shaft 14 includes an outer shaft tube 32 that may be constructed of a light weight metal material or may be a plastic material. The proximal end of the tube 32 is received by the adaptor cover 26. The distal end of the tube 32 is secured to the distal bendable member 20. Refer to FIG. 21 for some further details of the distal bendable member 20. Within the outer shaft tube 32 there is provided a support tube 34 that is preferably constructed of a plastic material. Tube 34 extends between the distal bendable or flexible member 20 and the proximal bendable or flexible member 18. The jaw actuator cable 38 extends within this support tube 34. The support tube 34, as depicted in FIG. 21, supports along its length a plurality of spacers 36. There may be five spacers disposed along the support tube 34. In the schematic diagram of FIG. 23 less than five are shown so as to simplify the diagram. Each of the spacers 36 is preferably evenly spaced and each is provided with diametric guide slots 37. In the embodiment disclosed herein there are four such guide slots disposed at 90 degree intervals about each spacer 36.

Refer also now to FIG. 21 for further details of the tool end of the instrument. The end effector 16 is comprised of a pair of jaws 44 and 46. As indicated previously these jaws may be used to grasp a needle 45 or other item. The upper jaw 44 fits within a channel 47 in the lower jaw 46. A pivot pin 48 is used between the jaws to enable rotation therebetween. A translation pin 42 extends through the slot 50 of jaw 46 and the slot 52 of jaw 44 and engages with the hole in the distal cable end connector 40. The connector 40 is secured to the very distal end of the jaw actuator cable 38 and is positioned within the channel 49 of the jaw 44. When the lever 22 is in its rest position, as depicted in FIG. 5, the jaws are fully open. In that position the pin 42 is at a more distal location maintaining the jaw in an open position. As the cable 38 is pulled, such as to the right in FIG. 6, then the pin 42 moves to the right in the slots 50 and 52 causing the jaws 44 and 46 to pivot toward a closed position as depicted in FIG. 6.

FIG. 21 also depicts an end wall 54 of the jaw 46. One end of the distal bendable member 20 is urged against this end wall 54. The member 20 may be secured to the wall 54 by an appropriate means. In the disclosed embodiment, the cabling tension itself of the instrument holds the members together. On the end wall 54 there are disposed a pair of anchors 56 and 58 for the flex control cables 100. FIG. 21 illustrates four such cables 100a, 100b, 100c and 100d. The distal end of the distal bendable member 20 is provided with pockets 59 for receiving the anchors 56 and 58. In this regard refer also to the cross-sectional view of FIG. 20 for an illustration of the position of the anchors 56 and 58. The anchors 56 and 58 are firmly attached to the end wall 54. FIG. 20 also illustrates the jaws closed with the translation pin 42 at the right end of the slots 50 and 52.

The jaw actuator cable 38 terminates at its respective ends at the end effector and the rotation barrel 66 (see FIG. 6). Within each of the bendable sections or bendable members 18 and 20 there is provided a plastic tube. This includes a distal tube 60 and a proximal tube 62. Both of these tubes may be constructed of a plastic such as polyethyletherkeytone (PEEK). The material of the tubes 60 and 62 is sufficiently rigid to retain the cable 38 and yet is flexible enough so that it can readily bend with the bending of the bendable members 18 and 20. The tubes have a sufficient strength to receive and guide the cable, yet are flexible enough so that they will not kink or distort, and thus keep the cable in a proper state for activation, and also defines a fixed length for the cable. The tubes 60 and 62 are longitudinally stiff, but laterally flexible.

Figure 19:
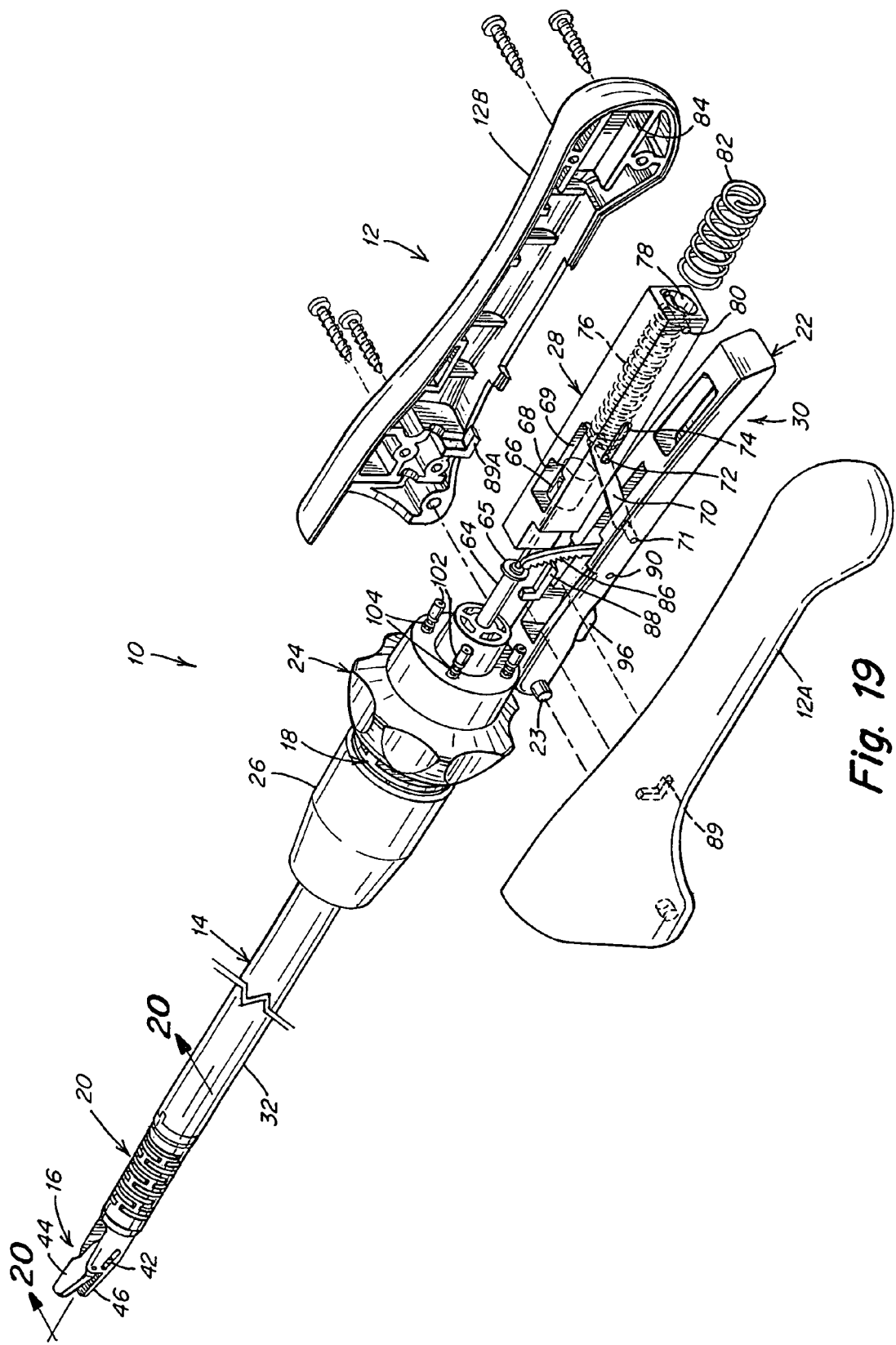
FIG. 19 is an exploded perspective view illustrating further details of the surgical instrument depicted in FIG. 1, particularly at the handle assembly.

FIG. 7 illustrates the proximal tube 62 extending within the proximal bendable member 18 between the support tube 34 and the rotation shaft 64. The jaw actuator cable 38 also extends through the rotation shaft 64. Refer also to FIG. 19 for an illustration of the rotational shaft 64. At either end of the shaft 64 is an E-ring 65 for securing the rotational shaft 64 in place. FIG. 19 illustrates the shaft 64 extending from the rotational knob 24 and the handle halves 12A and 12B that wrap around a part of the rotation knob 24. The opposite end E-rings 65 engage respectively with the handle and rotational knob and retain the rotational knob 24 in place relative to the handle 12, which, in turn, then retains the proximal bendable member in place relative to the handle. FIG. 7 shows the E-ring 65 on the left being disposed between an interior cavity of the knob 24 and a cavity in the proximal bendable member 18. The E-ring 65 on the right in FIG. 7 is captured by the handle 12.

The control of the end effector 16 is by means of the jaw actuator cable 38. The very proximal end of the jaw actuator cable 38 is retained in the rotational barrel 66. As illustrated, for example, in FIG. 7 the cable 38 is secured to the rotational barrel by means of a pair of set screws 67. The rotational barrel 66 is supported within the slider 28. More particularly, the rotational barrel 66 is disposed within the slider pocket 68. Refer also to FIG. 19 for an illustration of the barrel 66 and pocket 68. The slider 28 is also provided with a slot 69 that extends from the pocket 68 and accommodates the link 70. The link 70 is the main means for actuating the slider 28 and, in turn, the actuator cable 38 from the lever 22.

The actuation link 70 is supported at one end from the lever 22 by means of the pivot pin 71. The pivot pin 71 is disposed within a slot of the lever 22 as is depicted in FIG. 19. The opposite end of the link 70 is supported at another pin, referred to herein as slider pin 72. The pin 72 is retained for longitudinal movement in the slot 74 in the slider 28. FIG. 7 shows the respective pins 71 and 72 at the opposite ends of the link 70. FIG. 7 also illustrates the slider pin 72 urged against the actuator spring 76. The spring 76 is disposed within a compartment of the slider 28. The opposite end of the actuator spring 76 is retained by means of a retaining pin 80 that is disposed in the bore 78 that accommodates the spring 76. FIGS. 6, 7 and 19 also show the return spring 82 which is disposed within a bore 84 in the handle for accommodating the spring 82. One end of the spring 82 is urged against an interior wall of the handle and the opposite end of the spring is urged against an end wall of the slider 28. The spring 76 is a stronger spring than the spring 82 so that the spring 82 compresses first as the lever 22 is activated. Additional motion of the lever then causes the spring 76 to compress as the item is grasped. This dual spring arrangement prevents damage to the instrument cabling, particularly at the distal end of the instrument due to excessive forces imposed by the lever action.

The lever 22 actuates the end effector as it is pressed toward the handle body. The lever 22 operates with a ratchet and pawl arrangement with the lever capable of being depressed in ratcheted increments. This ratchet and pawl arrangement includes the ratchet 86 and pawl 88. To accommodate the ratchet 86, the slider 28 is provided with an end dish out or cut out 87, such as is illustrated in FIG. 5. The pawl 88 depicted also in FIG. 19 is retained by the handle members 12A and 12B. In this regard in handle part 12A there is a pocket 89 for the pawl 88 and in the handle part 12B there is provided a leg 89A for retaining the pawl. The ratchet 86 pivots at the pivot pin 90 and is provided with a series of ratchet teeth that can hold the ratchet in successive positions corresponding to successive degrees of closure of the end effector. A torsion spring 92 is disposed partially about the pivot 90 and urges the ratchet teeth into contact with the pawl 88 as illustrated in FIG. 7 in a fully closed position.

The ratchet and pawl arrangement also includes an integral release means that is usually engageable by the surgeons thumb. As depicted in FIG. 7, on one side of the pivot 90 there is the ratchet 86 and on the other side of the pivot there is the arm 94. A release button 96 is formed at the base of the arm 94. When a force is directed in the direction of arrow M in FIG. 7 then this releases the ratchet and pawl arrangement and returns the lever 22 to its released position with the jaws fully opened, as in FIG. 5.

Reference is flow made to the cabling that extends between the proximal and distal bendable members. This cabling is provided so that any bending at the proximal bendable member is converted into a corresponding bending at the distal bendable member. The bendable members that are described herein enable bending in all directions. In the preferred embodiment described herein, the distal bendable member is approximately ⅓ the diameter of the proximal bendable member as illustrated in FIG. 5. However, as indicated before other diameter relationships can be used depending upon the particular use of the instrument and the medical procedure in which it is being used.

The control between the proximal bendable member 18 and the distal flexible member 20 is carried out by means of the flex control cables 100. There are four such cables identified, for example, in FIG. 21 as cables 100A, 100B, 100C and 100D. At the distal end of these cables, as has been described hereinbefore, the cables connect to the anchors 56 and 58 at the jaws. Cables 100 are retained at their proximal ends by cable end lugs 102. Four springs 104 are retained between these end lugs 102 and a wall of the rotation knob 24. Refer to FIG. 19 for an illustration of the end lugs 102 and the springs 104. The springs 104 tension or take up the slack on the cables. Between the bendable members, the cables 100 are guided by means of the slots 37 in the spacers 36 along the support tube 34. Refer also to FIGS. 23 and 24. Within the adaptor cover 26, the cables 100 extend through the transition member 106. The cables then extend to a larger outer diameter locus as they extend through the proximal bendable member as depicted in FIGS. 6 and 7. The stepped transition member 106 may be of metal and is secured to the end of tube 32.

FIG. 21 depicts the distal end of the instrument and, in particular, the distal flexible member 20. This is in the form of a single piece slotted structure comprised of alternating slots and discs. The discs are supported from a central member defining the bore 120. FIGS. 21 and 22 illustrate the discs 110 that define therebetween the annular slots 112. Between adjacent discs there are also provided connecting ribs 111. Clearance holes 114 are provided for receiving the cables 100. These clearance holes are provided in the ribs and discs. To align the distal flexible member with the shaft tube 32, there is provided an alignment tab 116 on the distal bendable member 20 and a corresponding slot 118 in the tube 32. One tab and slot arrangement is illustrated in FIG. 21, however, it is understood that more than one tab and slot may be provided The distal bendable member 20 also has a central bore 120 for receiving the aforementioned PEEK tube 60.

The proximal bendable member 18 is also constructed as a unitary or uni-body slotted structure including a series of flexible discs 130 that define therebetween slots 132. A "unitary" or "uni-body" structure may be defined as one that is constructed for use in a single piece and does not require assembly of parts. Connecting ribs 131 extend between the discs. Clearance holes 134 are provided for accommodating the cables 100. As with the distal bendable member, the proximal bendable member also includes alignment tabs 136 and corresponding slots (not shown) in the rotation knob 24. The proximal bendable member 18 is also provided with a central bore 140 for receiving the tube 62

Both of the bendable members preferably have a rib pattern in which the ribs (111, 131) are disposed at a 60 degree variance from one rib to an adjacent rib. This has been found to provide an improved bending action. It was found that by having the ribs disposed at intervals of less than 90 degrees therebetween improved bending was possible. The ribs may be disposed at intervals of from about 35 degrees to about 75 degrees from one rib to an adjacent one. By using an interval of less than 90 degrees the ribs are more evenly distributed. As a result the bending motion is more uniform at any orientation. In the present invention both of the bendable members may be made of a highly elastic polymer such as PEBAX (Polyether Block Amide), but could also be made from other elastic materials.

FIGS. 5-7 illustrate a sequence of operation of the surgical instrument, including in particular the tool actuation that is controlled by the actuation lever 22. In the illustrated example employing a pair of jaws, there is provided a dual spring arrangement (springs 76 and 82) that enables the grasped item to be securely held by the jaws. Reference is now made to FIG. 5 for an illustration of the surgical instrument in which the lever 22 is at its fully released (down) position corresponding to the jaws 44 and 46 being in a fully open position. At any time the release button 96 may be depressed to move the lever 22 to that position. In that position the springs 76 and 82 are in their expanded or relaxed position and the ratchet 86 is at its top end of travel with the pawl engaging a top tooth of the ratchet.

The cross-sectional view of FIG. 6 illustrates the lever 22 being depressed further. This is illustrated by the arrow H in FIG. 6. The depression of the lever 22 causes a corresponding motion of the link 70. This motion imparts a force to the spring 72. However, spring 76 is a stiffer spring than spring 82 and thus in the position illustrated in FIG. 6 the slider pin 72 is maintained to the left of the slot 74. At the position of FIG. 6 substantially only the larger diameter spring 82 is compressed. This is illustrated by the arrow I. In this position it is also noted that the ratchet has now moved to a position approximately mid-point of its teeth at ratchet 86 relative to the pawl 88. This action represents the state where the jaws are just beginning to exert a force on the needle. This is illustrated by the arrow J in FIG. 6, indicating movement of the jaws to a more closed position for grasping the needle 45.

At the position illustrated in FIG. 6, the spring 82, having a smaller poundage than the spring 76, compresses when the force on the lever is approximately 3 to 4 pounds. In the position of FIG. 6, even though the needle 45 has been grasped, the spring 76 is substantially non-compressed at that stage, but is pre-loaded from the spring 82.

Reference is now made to FIG. 7 for an illustration of the lever 22 having been moved to a position in which the spring pressure imposes a tightening of the item that is being grasped. In FIG. 7 the arrow K illustrates the further lever movement loading the spring pressure on the jaws. This additional lever rotation causes the slider pin 72 to slide within the slot 74 further compressing the spring 76. This is illustrated in FIG. 7 by the arrow L. This imposes an additional force on the slider 28 causing the actuator cable 38 to tightly close the jaws about the needle 45. FIG. 7 also illustrates by the arrow M the release sequence in which the button 96 may be pressed to release the ratchet 86 from the pawl 88 and thereby return the lever arm 22 to the position illustrated in FIG. 5.

Reference is now made to FIGS. 9-18. These figures are successive cross-sectional views taken from FIG. 6 and showing further cross-sectional details of components of the surgical instrument. The cross-sectional view of FIG. 8 is a longitudinal cross-section illustrating the top of the slider 28. The cross-sectional view of FIG. 9 is taken at the jaws 44 and 46 and further illustrates the slide pin 42 controlled to move in the slots 50 and 52 by engagement with the distal cable end connector 40.

The cross-sectional view of FIG. 10 illustrates the anchors 56 and 58 for the flexible cables as well as the tool actuator cable 38 disposed within the tube 60.

FIG. 11 is a cross-sectional view taken through the distal bendable member 20. FIG. 11 also illustrates the actuator cable 38, tube 60 and the position of the ribs 111. It is apparent from FIG. 11 that the ribs 111 are disposed, from one to the other, at an angle of approximately 60 degrees. These ribs are preferably disposed at an angle of less than 90 degrees.

FIG. 12 is a cross-sectional view taken through the instrument shaft. This view illustrates the support tube 34 having the actuator cable 38 therein. This view also illustrates the outer shaft tube 32 and the flex control cables 100.

FIG. 13 is a cross-sectional view taken at the adaptor cover 26 where the control cables transition between the instrument shaft and the proximal bendable member 18. FIG. 13 illustrates the four flex control cables 100A, 100B, 100C and 100D so transitioning. FIG. 13 also illustrates one of the spacers 36 with its associated guide slots.

FIG. 14 is a cross-sectional view taken directly through the proximal bendable member 18. This illustrates the disks 130 and the interconnecting ribs 131. Clearance holes 134 are illustrated for receiving the control cables 100. As with the distal bendable member, the proximal bendable member has its ribs disposed at 60 degree intervals from one rib to the next. These ribs are preferably disposed at an angle of less than 90 degrees. The clearance holes 134 are preferably diametrically disposed as illustrated in FIG. 14. FIG. 14 also illustrates the angular relationship between the ribs as angle θ, and the interrelationship regarding the clearance holes as the angle β. The angle β is shown at 90 degrees.

FIG. 15 is a further cross-sectional view that is taken essentially at the proximal end of the rotation knob 24. This illustrates the cable end lugs 102, the actuation cable 38 and the rotation shaft 64. It is also noted in FIG. 15 that the same arrows are used therein as previously described in connection with FIG. 4. Thus, in FIG. 15 the arrow R1 indicates rotation of the knob 24 while the arrow R2 indicates rotation of the instrument shaft. The rotation knob 24, as illustrated, includes a plurality of indentations 24A. These are preferably arcuate as shown and define therebetween peaks 24B. This surface is configured so that the thumb of the user can readily rotate the knob 24 by engagement of the thumb with one or more of the knob indentations 24A.

The cross-sectional view of FIG. 16 illustrates the ratchet and pawl locking action for the spring tensioning of the actuator cable 38. FIG. 16 illustrates the ratchet 86, the pawl 88, the release button 96, the torsion spring 92, and the rotation shaft 64 with its associated E-ring 65. FIG. 16 also illustrates the release button 96.

FIG. 17 is a cross-sectional view showing the rotating barrel means that is used to prevent torsional forces on the actuator cable 38. The slider 28 has a pocket 68 for accommodating the rotational barrel 66. FIG. 17 also shows a set screw 67 for attaching the actuator cable 38 to the rotational barrel 66.

Finally, the cross-sectional view of FIG. 18 shows further details of the spring loading means. This includes the spring 76, slider 28, lever 22, and link 70.

Reference is now made to FIG. 22. FIG. 22 is a cross-sectional view that focuses on the proximal and distal bendable members particularly as to the relationship between the bending angles that are preferred. Regarding the proximal bendable member 18, this is illustrated as being bent through an angle B1. The distal bendable member 20 is illustrated as being bent through an angle B2. By way of example, the angle B1, if at a 35 degree, corresponds with a distal bendable angle B2 of approximately 70 degrees. Thus, it can be seen that the difference in diameter between the bendable members enables a greater degree of bending at the distal end for a corresponding bending at the proximal end. Although this illustrated diameter relationship for the bendable members is preferred, it should be understood that other variations may be used, including the use of the same diameters at the proximal and distal ends of the instrument or even using a larger diameter at the distal end corresponding to a smaller diameter at the proximal end.

Reference is now made to the schematic diagrams of FIGS. 23 and 24. The schematic diagram of FIG. 23 corresponds to the instrument motions depicted in FIGS. 3a-3c. The schematic diagram of FIG. 24 corresponds to the instrument motions depicted in FIGS. 2a-2c. In FIG. 23 the instrument shaft 14 is illustrated as containing a series of spacers 36 having associated guide slots 37 for positioning each of the control cables 100. In this embodiment the control cables extend in a straight orientation while in FIG. 24 the control cables are twisted through 180 degrees.

In FIG. 23 at the distal end of the instrument, the control cables are identified as cables 100A, 100B, 100C and 100D. At the proximal end of the instrument, the same cables are identified as cables 100A', 100B', 100C' and 100D'. This straight alignment of the cables results in a relationship between the proximal and distal bendable members as illustrated in FIGS. 3a-3c. In other words, when the handle end is moved up the tool end moves down and vice versa. In the schematic diagram of FIG. 24, the same number of spacers 36 may be employed. In an actual instrument that has been constructed five such spacers have been used, although, for simplicity in FIGS. 23 and 24 only three spacers are shown. In the embodiment of FIG. 24 the control cables 100 are twisted 180 degrees as they progress from one end of the instrument shaft to the other. Thus, for example, a proximal cable 100' at the proximal end of the instrument is twisted so that the cable 100 at the distal end of the instrument is displaced by 180 degrees. This creates a related bending between the proximal end-distal ends of the instrument as is illustrated in FIGS. 2a-2c. In other words, when the handle end is moved up the tool end moves up and vice versa.

Regardless of which embodiment is used, either the one in FIG. 23 or the one in FIG. 24, the actuator cable 38 operates in substantially the same way. Operation of the lever 22 pulls the cable in a direction of arrow I in FIG. 6, closing the end effector. Release of the lever moves the cable in the opposite direction. Both actions occurs in the normal position of the instrument such as in FIG. 3a or in other deflected positions such as in FIGS. 3b and 3c where the proximal bendable member 18 controls the distal bendable member 20. In this regard, the cable 38 is preferably supported centrally in the instrument shaft as well as in the bendable members as illustrated in the drawings herein. In this way, when a bending occurs there is no significant movement imparted to the cable 38 by the bending action. In other words, the end effector actuation is de-coupled from the bending action.

The rotation of the knob 24 also occurs without effecting the bending and tool actuation actions. This rotation action is also de-coupled from these other actions or motions. For example, rotation of the knob 24, in and of itself, does not effect tool actuation or bending actions. Regardless of the position of the lever 22 or the degree of bending at the proximal bendable member, any rotation at the knob 24 imparts a like rotation to all of the components distal of the knob 24 including the instrument shaft 14, the end effector 16 and the proximal and distal bendable members 18 and 20 while maintaining the orientation at the distal end bendable section. As the components are rotated from the knob 24, the cable 38 will rotate therewith. The rotating barrel means, namely the barrel 66, prevents torsional forces on the tool actuator cable. The rotational barrel 66, which is secured to the very proximal end of the actuator cable 38, is rotatable within the slider 28 so that the cable readily rotates with the rotation of the knob 24. It is noted that the direction of the bend (orientation) of the distal bendable member is not effected by the rotation at the knob 24. This rotation simply rotates the distal motion member on its own axis without changing orientation.

Another aspect of the surgical instrument of the present invention relates to the ease with which the surgeon can manipulate the instrument in effectively performing a surgical procedure. The placement of the rotation knob 24 in close proximity to the handle 12 and proximal bendable member 18 makes manipulation easier. It is advantageous to have a part of the proximal bendable member 18 disposed within a hollow center of the rotation knob 24 as is clearly shown in FIGS. 6 and 7. The hollow area is formed by a tapered wall 25 (see FIGS. 7 and 22) that enables bending or deflection of the proximal bendable member 18, such as is illustrated in FIG. 22 where the proximal bendable member 18 is at one extreme of bending. The knob 24 is also shown rotationally supported adjacent to the handle 12 so that it is in a convenient position for use by the surgeon.

The axial rotation knob 24 is rotatably mounted on the tube 64, which in turn is clamped to the handle body. As a result the axial rotation knob is able to freely rotate relative to the handle body, manipulated by either the thumb or index finger, instead of rotating the entire handle assembly. The axial rotation knob 24 has the tapered or conical cavity in which the proximal bendable member is mounted for motion with the knob. In order to maintain maximum control of the distal tool, the proximal bendable member is disposed at least partially within the conical cavity in the axial rotation knob 24 thereby minimizing the distance between the knob and the user's hand. If the proximal bendable member is situated too far from the handle this can give the user a feeling of floppiness in the use of the instrument. Accordingly, by disposing the proximal bendable member at least partially within the knob one minimizes this sloppiness. This placement also enables the instrument shaft to be closer to the user's hand. There may be instances where the user wants to control the instrument by directly applying pressure to the instrument shaft rather than through the bendable member. In such case the user would lean their index finger on the finger support sleeve 26 which would allow the user to apply force directly on the instrument shaft.

As indicted hereinbefore and as depicted in FIG. 4 the surgeon is able to roll the instrument's tool about its longitudinal axis at any orientation (bent position) simply by rolling the axial rotation knob 24. FIGS. 25-28 illustrate the sequential positions of the rotation knob 24 and the corresponding orientation of the tool 16, rotated about the tool axis P. The direction or orientation of the bend (angle B2) of the distal bendable member, relative to the shaft axis Z, is not effected by the rotation at the knob 24. As can be seen from the sequence of FIGS. 25-28, this rotation simply rotates the distal motion member and tool on its own distal motion axis P without changing the orientation of the tool. The orientation is only affected by the bending action.

The instrument schematically illustrated in FIGS. 25-28 may be the same instrument as described hereinbefore in FIGS. 1-24. In FIGS. 25-28 the bendable members are considered as being maintained in a particular position corresponding to the same respective proximal and distal bendable member angles B1 and B2. The respective FIGS. 25-28 show the rotation knob 24 in successive 90 degree positions and the manner in which the motion imparted to the rotation knob is transferred to the distal bendable member and tool. From position to position the orientation of the tool along axis P is maintained the same. In one example in FIGS. 25-28 the angle B1 may be 25 degrees and the angle B2 may be 35 degrees. The angle B1 is measured between axis T of the handle and the main instrument axis Z, while angle B2 is measured between the distal tool axis P and the axis Z.

The control between the proximal bendable or flexible member 18 and the distal bendable or flexible member 20 is carried out by means of the flex control cables 100. There are four such cables identified as cables 100A, 100B, 100C and 100D. At the distal end of these cables, as has been described hereinbefore, the cables connect to the anchors 56 and 58 at the jaws. Cables 100 are retained at their proximal ends by cable end lugs 102. Four springs 104 are retained between these end lugs 102 and a wall of the rotation knob 24. FIGS. 25-28 illustrate the cable ends by the proximal ends 100A', 100B', 100C' and 100D', and by the distal ends 100A", 100B", 100C" and 100D".

FIG. 25 also depicts the rolling motion that can be carried out with the instrument of the present invention. This occurs by virtue of the rotation of the rotation knob 24 relative to the handle 12 about axis T. This is illustrated in FIG. 25 by the circular arrow R1. When the rotation knob 24 is rotated, in either direction, this causes a corresponding rotation of the instrument shaft 14 about axis Z. This is depicted in FIG. 25 by the rotational arrow R2. This same motion also causes a rotation of the end effector 16 about axis P as illustrated by the rotational arrow R3. FIGS. 25-28 also show a proximal coordinate at Q at the proximal cable ends and a distal coordinate at U at the distal cable ends. The directional arrows N(north); W(west); S(south) and E(east) depict the sequential rotation of the rotation knob 24 in these coordinate systems, and as relates to the state of the cabling between the proximal and distal members of the instrument.

FIG. 25 depicts an initial position of the instrument with the bendable members 18 and 20 in a certain position. For the sake of clarity in describing the operation the bendable members are considered as being maintained in the same bent condition and only the knob rotation is considered as changing during the sequence from FIG. 25 to FIG. 28. Of course, in practice the instrument functions with the ability to bend in any direction and to roll the tool about axis P through any angle in performing an actual medical procedure. Also, even though only 90 degree intervals are described in relationship to FIGS. 25-28, it is understood that the same distal rotation about axis P occurs for all intermediate positions. Also, four cables are depicted in the illustrated embodiments, however, fewer or more then four may be used In FIG. 25 the handle 12, via proximal bendable member 18, is shown tilted along axis T at an angle B1. This tilting or bending may be considered as in the plane of the paper. By means of the cabling 100 this action causes a corresponding bend at the distal bendable member 20 to a position wherein the tip is directed along axis P and at an angle B2. This distal bending is also considered as in the plane of the paper. The cabling 100 is depicted wherein two of the cables are considered in tension and the other two are relaxed. In the position depicted the rotation knob 24 may be considered as in the initial position N. In that position the cables 100A and 100B are in their relaxed state while cables 100C and 100D are in their tensioned state. This causes a bending down of the instrument tip in response to the handle being bent or pivoted upwardly, as shown.

The rotation knob 24 is then rotated through 90 degrees to the position W depicted in FIG. 26. This rotates the position of the cables so that the cables 100B and 100C are in their relaxed state while cables 100A and 100D are in their tensioned state. This action maintains the same orientation of the tool 16 along axis P, but rotates the distal bendable member and tool about the axis P. Both ends of the instrument are maintained in the plane of the paper. The rotation of the tool is depicted by the jaws having been rotated through 90 degrees, as can be seen by a comparison of FIGS. 25 and 26. The orientation along axis P is maintained.

The rotation knob 24 is then rotated through 90 degrees to the position S depicted in FIG. 27. This rotates the position of the cables so that the cables 100C and 100D are in their relaxed state while cables 100A and 100B are in their tensioned state. This action maintains the same orientation of the tool 16 along axis P, but rotates the tool about the axis P. Both ends of the instrument are maintained in the plane of the paper. The rotation of the tool is depicted by the jaws having been rotated through 90 degrees, as can be seen by a comparison of FIGS. 26 and 27. The orientation along axis P is maintained.

The rotation knob 24 is then rotated through 90 degrees to the position E depicted in FIG. 28. This rotates the position of the cables so that the cables 100A and 100D are in their relaxed state while cables 100B and 100C are in their tensioned state. This action maintains the same orientation of the tool 16 along axis P, but rotates the tool about the axis P. Both ends of the instrument are maintained in the plane of the paper. The rotation of the tool is depicted by the jaws having been rotated through 90 degrees, as can be seen by a comparison of FIGS. 27 and 28. The orientation along axis P is maintained.

In the disclosed embodiments the rotation knob is illustrated as a knob having indentations for the finger or fingers. In alternate embodiments of the invention the rotation function may be performed by other means such as a rotation wheel or a rotatable lever.

Still another aspect of the surgical instrument of the present invention is the ability to adapt the instrument to a wide variety of medical procedure. This includes, but is not limited to, access to a body cavity such as through an incision or intraluminal use such as through a natural body aperture to a body lumen. The introduction of the surgical instrument into the anatomy may also be by percutaneous or surgical access to a lumen, cavity or vessel, or by introduction through a natural orifice in the anatomy.

There are several improvements brought forth by employing bendable sections for the motion members particularly as opposed to other mechanisms such as pivotal joints or ball-and-socket joints.

A first important attribute of a bendable member is in its inherent lateral (bending) stiffness, especially when used for the proximal handle motion member. In a jointed arrangement the proximal joint is situated between the elongated shaft and the control handle, together with the fulcrum at the incision. This behaves as a "double-joint" and the instrument may have a serious tool stability issue if the joint is "free" to move. Suppose the operating surgeon slightly moves his/her wrist while holding the control handle of the instrument. If the joint is "free" to move without providing substantial support resistance, due to the fulcrum effect of the long elongated shaft passing through the incision, it will result in substantial, unintended swinging of the tool end of the instrument in opposite direction. In a typical laparoscopic or endoscopic procedure where the operating field is small, such instability of the tool will render the tool potentially dangerous and unusable. Unlike the pivotal or ball-and-socket joints that are "free" to move, a bendable member has inherent stiffness which acts to provide necessary support for stabilizing the operator hand's wrist movement, which in turn stabilizes the tool motion. By varying the material and geometry of the bendable member, the appropriate level of stability could be selected.

A second important attribute of the bendable member, especially for bending in two degrees of freedom, is its uniformity in bending. Because the bendable member can bend in any direction uniformly, it has no inherent singularity, and as the result, the operator can produce uniform rolling motion of the tool, an important motion for tasks such as suturing, simply by rolling the control handle. On the other hand, if the motion members are comprised of series of pivotal joints, not only may it bind due to singularities, but the rolling of the control handle will result in unwanted side motion of the tool as well, affecting its usability for surgical procedure.

A third attribute of the bendable member is its ability to transmit substantial torque axially. By selecting appropriate material and geometry, the bendable member can be constructed to transmit torque axially necessary to perform a surgical procedure. On the other hand, the motion member comprised of ball-and-socket joints will not be able to transmit the necessary torque from the handle to the tool end.

A fourth attribute of the bendable member is that it has no sharp bending point, location or pivot and thus this results in an increased life and higher performance. Either pivotal or ball-and-socket joints on the other hand have sharp corners which can increase friction, reduce life and decrease performance of the tool actuation push rod passing through.

A fifth attribute of the bendable member is in the reduction of manufacturing cost. The bendable motion member can be injection molded as a single body, thus significantly reducing the cost. Pivotal or ball-and-socket joints are comprised of more parts and this results in a higher manufacturing cost.

Lastly, a sixth attribute of the bendable member is that it can be easily customized. By varying the stiffness at different points of the bendable member, one can optimize its bending shape for specific applications.

While this invention has been particularly shown and described with references to preferred embodiments thereof, it will be understood by those skilled in the art that various changes in form and details may be made therein without departing from the scope of the invention encompassed by the appended claims. For example, the embodiments described herein have primarily used four control cables for providing all direction motion of the motion members. In alternate embodiments fewer or greater numbers of cables may be provided. In a most simplified version only two cables are used to provide single DOF action at the bendable motion member. Also, the disclosed embodiment uses a handle that is essentially in line with the instrument shaft. In an alternate embodiment of the invention the handle can be off axis or at an angle to the instrument shaft in the rest position of the instrument.

What is claimed is:

1. A manually operated medical instrument having an instrument shaft that couples with an operating handle at a proximal end thereof and a tool at a distal end thereof, further comprising a proximal bendable member at the proximal end of the instrument shaft that is bendable into a curved configuration, a distal bendable member at the distal end of the instrument shaft that is bendable into a curved configuration, and one or more actuating elements intercoupling the proximal and distal bendable members responsive to a manually initiated bending at the proximal bendable member to cause a corresponding bending into a curved configuration of the distal bendable member so as to control, via the handle, the positioning of the tool.

2. The instrument of claim 1 wherein the bendable members are bendable in all directions.

3. The instrument of claim 1 wherein the bendable members are bendable in any direction.

4. The instrument of claim 1 wherein the proximal bendable member is manipulated in any direction do that the distal bendable member is controlled in three dimensions.

5. The instrument of claim 1 further including a rotation knob disposed between said handle and proximal bendable member.

6. The instrument of claim 5 wherein said rotation knob is supported to rotate the proximal bendable member therewith.

7. The instrument of claim 6 wherein rotation of the rotation knob controls the tool for corresponding rotation about a tool axis.

8. The instrument of claim 6 wherein said tool is disposed from said distal bendable member along a longitudinal distal tool axis, the rotation of said rotation knob causing a corresponding rotation of said tool about said distal tool axis.

9. The instrument of claim 6 wherein said one or more actuating elements comprises a set of actuation cables and wherein at least one of said set is in tension while at least another one thereof is in relaxation.

10. The instrument of claim 9 including four cables disposed at 90 degree intervals about the instrument shaft with two in tension and two in relaxation during a bending.

11. The instrument of claim 5 wherein the instrument shaft comprises an elongated instrument shaft extending along a longitudinal axis and wherein the distal bendable member is disposed in-line with the elongated instrument shaft coupling a distal end of said elongated instrument shaft to said tool and wherein the proximal bendable member is disposed in line with the elongated instrument shaft coupling a proximal end of said elongated instrument shaft via said rotation knob to said handle.

12. A surgical instrument comprising:
   an elongated instrument shaft having proximal and distal ends;
   a working member disposed from the distal end of the instrument shaft; and
   a control handle disposed from the proximal end of the instrument shaft;
   a distal bendable member capable of bending into a curved configuration;
   said working member being coupled to the distal end of said elongated instrument shaft via said distal bendable member;
   a proximal bendable member capable of bending into a curved configuration;
   said control handle coupled to the proximal end of said elongated instrument shaft via a proximal bendable member;
   a manually rotatable member arranged adjacent the control handle and between the control handle and proximal bendable member;
   said rotatable member adapted to be manually rotated to, in turn, rotate the instrument shaft, distal bendable member and working member relative to said control handle;
   and an actuation element extending between said distal and proximal bendable members whereby any deflection of said control handle with respect to said elongated instrument shaft causes a corresponding bending of said distal motion member for control of said working member.

13. The surgical instrument of claim 12 wherein said rotatable member comprises a rotation knob having a cavity for receiving at least a portion of said proximal bendable member therein and at least a portion of said rotation knob is received by said handle in an open end of said handle, said rotation knob having said proximal bendable member supported therein and in a fixed relative rotation with respect to said proximal bendable member.

14. The surgical instrument of claim 12 wherein said working member comprises a tool that is supported from said distal bendable member extending along a distal tool axis and said rotatable member comprises a rotation knob, the rotation of said rotation knob causing a rotation of said working member about said distal tool axis.

15. The surgical instrument of claim 14 wherein the rotation of said rotation knob rotates the instrument shaft and distal bendable member, rotating the tool about the distal tool axis while maintaining the orientation of the tool.

* * * * *